(12) United States Patent
Cabiri et al.

(10) Patent No.: US 9,987,432 B2
(45) Date of Patent: Jun. 5, 2018

(54) ROTATION RESISTANT FRICTION ADAPTER FOR PLUNGER DRIVER OF DRUG DELIVERY DEVICE

(71) Applicant: MEDIMOP Medical Projects Ltd., Ra'anana (IL)

(72) Inventors: Oz Cabiri, Macabim-Reut (IL); Ran Hezkiahu, Herzliya (IL)

(73) Assignee: West Pharma. Services IL, Ltd., Ra'anana (IL)

(*) Notice: Subject to any disclaimer, the term of this patent is extended or adjusted under 35 U.S.C. 154(b) by 152 days.

(21) Appl. No.: 14/861,478

(22) Filed: Sep. 22, 2015

(65) Prior Publication Data
US 2017/0080158 A1    Mar. 23, 2017

(51) Int. Cl.
*A61M 5/315*    (2006.01)
*A61M 5/142*    (2006.01)
*A61M 5/31*    (2006.01)

(52) U.S. Cl.
CPC ........ *A61M 5/31515* (2013.01); *A61M 5/142* (2013.01); *A61M 5/31586* (2013.01); *A61M 2005/3123* (2013.01)

(58) Field of Classification Search
CPC ........... A61M 2005/3151; A61M 2005/31508; A61M 2005/31598; A61M 5/31505; A61M 5/31568; A61M 5/31578
See application file for complete search history.

(56) References Cited

U.S. PATENT DOCUMENTS

| | | |
|---|---|---|
| 232,432 A | 9/1880 | Allison |
| 1,795,630 A | 3/1931 | Wilson |
| 2,677,373 A | 5/1954 | Barradas |
| 2,702,547 A | 2/1955 | Glass |
| 2,860,635 A | 11/1958 | Wilburn |
| 3,203,269 A | 8/1965 | Perrine |
| 3,212,685 A | 10/1965 | Swan et al. |

(Continued)

FOREIGN PATENT DOCUMENTS

| | | |
|---|---|---|
| CN | 1505535 A | 6/2004 |
| CN | 1747683 A | 3/2006 |

(Continued)

OTHER PUBLICATIONS

Int'l Search Report and Written Opinion dated Jul. 6, 2017 in Int'l Application No. PCT/US2017/022966.

(Continued)

*Primary Examiner* — Laura Bouchelle
*Assistant Examiner* — Tasnim M Ahmed
(74) *Attorney, Agent, or Firm* — Panitch Schwarze Belisario & Nadel LLP

(57) ABSTRACT

A method and system are disclosed for driving a plunger in a drug reservoir. In some embodiments, a variable friction element interconnects between a pushing shaft and a wall of the reservoir. For example, rotation of a driving element in a first direction relative to the pushing shaft may advance the pushing shaft in the reservoir. The friction element may have increased friction resistance to rotation of the pushing shaft in the first direction in comparison to frictional resistance to advancing the pushing shaft. For example, the increased friction may result from wedging a radial element between the pushing shaft and the wall of the reservoir.

15 Claims, 22 Drawing Sheets

(56) References Cited

U.S. PATENT DOCUMENTS

| | | | |
|---|---|---|---|
| 3,623,474 A | 11/1971 | Heilman et al. |
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,564,054 A | 1/1986 | Gustavsson |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,664,654 A | 5/1987 | Strauss |
| 4,685,903 A | 8/1987 | Cable et al. |
| 4,698,055 A | 10/1987 | Sealfon |
| 4,735,311 A | 4/1988 | Lowe et al. |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,892,521 A | 1/1990 | Laico et al. |
| 4,919,569 A | 4/1990 | Wittenzelliner |
| 4,919,596 A | 4/1990 | Slate et al. |
| 4,929,241 A | 5/1990 | Kulli |
| 4,950,246 A | 8/1990 | Muller |
| 4,964,866 A | 10/1990 | Szwarc |
| 5,051,109 A | 9/1991 | Simon |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,318,522 A | 6/1994 | D'Antonio |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |
| 5,562,686 A | 10/1996 | Sauer et al. |
| 5,593,390 A | 1/1997 | Castellano et al. |
| 5,616,132 A | 4/1997 | Newman |
| 5,624,400 A | 4/1997 | Firth et al. |
| 5,637,095 A | 6/1997 | Nason et al. |
| 5,643,218 A * | 7/1997 | Lynn ............... A61M 5/002 604/191 |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Osterlind et al. |
| 5,690,618 A | 11/1997 | Smith et al. |
| 5,728,075 A | 3/1998 | Levander |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,989,221 A | 11/1999 | Hjertman |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,045,533 A | 4/2000 | Kriesel et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,554,800 B1 | 4/2003 | Nezhadian et al. |
| 6,558,351 B1 | 5/2003 | Steil et al. |
| 6,565,541 B2 | 5/2003 | Sharp |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |

(56) References Cited

U.S. PATENT DOCUMENTS

| | | |
|---|---|---|
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,033,338 B2 | 4/2006 | Vilks et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,066,909 B1 | 6/2006 | Peter et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,442,186 B2 | 10/2008 | Blomquist |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | DiBiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,766,867 B2 | 8/2010 | Lynch et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 * | 6/2011 | Cabiri ............... A61M 5/14566 604/154 |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,348,898 B2 | 1/2013 | Cabiri |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,523,803 B1 | 9/2013 | Favreau |

(56) References Cited

U.S. PATENT DOCUMENTS

| | | |
|---|---|---|
| 8,551,046 B2 | 10/2013 | Causey et al. |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,622,966 B2 | 1/2014 | Causey et al. |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,915,882 B2 | 12/2014 | Cabiri |
| 8,920,374 B2 | 12/2014 | Bokelman et al. |
| 8,979,802 B2 | 3/2015 | Woehr |
| 9,011,164 B2 | 4/2015 | Filman et al. |
| 9,061,104 B2 | 6/2015 | Daniel |
| 9,061,110 B2 | 6/2015 | Avery et al. |
| 9,072,827 B2 | 7/2015 | Cabiri |
| 9,089,475 B2 | 7/2015 | Fangrow |
| 9,089,641 B2 | 7/2015 | Kavazov |
| 9,149,575 B2 | 10/2015 | Cabiri |
| 9,173,997 B2 | 11/2015 | Gross et al. |
| D747,799 S | 1/2016 | Norton et al. |
| 9,259,532 B2 | 2/2016 | Cabiri |
| 9,314,569 B2 | 4/2016 | Causey et al. |
| 9,345,836 B2 | 5/2016 | Cabiri et al. |
| 9,350,634 B2 | 5/2016 | Fadell |
| 9,393,365 B2 | 7/2016 | Cabiri |
| 9,421,323 B2 | 8/2016 | Cabin et al. |
| 9,452,261 B2 | 9/2016 | Alon |
| 9,522,234 B2 | 12/2016 | Cabiri |
| 9,539,388 B2 | 1/2017 | Causey et al. |
| 9,572,926 B2 | 2/2017 | Cabiri |
| 9,656,019 B2 | 5/2017 | Cabiri et al. |
| 9,782,545 B2 | 10/2017 | Gross et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2003/0009133 A1 | 1/2003 | Ramey |
| 2003/0014018 A1 | 1/2003 | Giambattista et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0216683 A1 | 11/2003 | Shekalim |
| 2004/0000818 A1 | 1/2004 | Preuthun et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186441 A1 | 9/2004 | Graf et al. |
| 2004/0210196 A1 | 10/2004 | Bush, Jr. et al. |
| 2004/0260233 A1 | 12/2004 | Garibotto et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Paulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0206054 A1 | 9/2006 | Shekalim |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |

(56) References Cited

U.S. PATENT DOCUMENTS

| | | |
|---|---|---|
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1* | 4/2009 | Gross ............... A61M 5/14248 604/518 |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Bruggemann et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Bruggemann et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0190693 A1 | 7/2013 | Ekman et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0267895 A1* | 10/2013 | Hemmingsen .......... A61M 5/24 604/93.01 |
| 2013/0296799 A1 | 11/2013 | Degtiar et al. |
| 2013/0304021 A1 | 11/2013 | Cabiri et al. |
| 2013/0310753 A1 | 11/2013 | Cabiri |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |

(56) References Cited

U.S. PATENT DOCUMENTS

| | | |
|---|---|---|
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |
| 2015/0119798 A1 | 4/2015 | Gross et al. |
| 2015/0374926 A1 | 12/2015 | Gross et al. |
| 2016/0030665 A1 | 2/2016 | Cabiri |
| 2016/0296716 A1 | 10/2016 | Cabiri et al. |
| 2016/0346478 A1 | 12/2016 | Bar-El et al. |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 201692438 U | 1/2011 |
| CN | 201941304 U | 8/2011 |
| CN | 102186733 A | 9/2011 |
| CN | 102378638 A | 3/2012 |
| DE | 1064693 B | 9/1959 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 1003581 B1 | 11/2000 |
| EP | 1219312 A2 | 7/2002 |
| EP | 1530979 A1 | 5/2005 |
| EP | 1666080 A1 | 6/2006 |
| EP | 2060606 A1 | 5/2009 |
| EP | 2498589 A1 | 9/2012 |
| FR | 2770136 A1 | 4/1999 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 200130421 A2 | 5/2001 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 0272182 A1 | 9/2002 |
| WO | 03090833 A1 | 11/2003 |
| WO | 04000397 A1 | 12/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2005072795 A2 | 8/2005 |
| WO | 2006037434 A1 | 4/2006 |
| WO | 06069380 A1 | 6/2006 |
| WO | 2006102676 A1 | 9/2006 |
| WO | 2006104806 A2 | 10/2006 |
| WO | 2006121921 A2 | 11/2006 |
| WO | 2007017052 A1 | 2/2007 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2010089313 A1 | 8/2010 |
| WO | 2011075105 A1 | 6/2011 |
| WO | 2011090955 A1 | 7/2011 |
| WO | 2011090956 A2 | 7/2011 |
| WO | 2011156373 A1 | 12/2011 |
| WO | 2012032411 A2 | 3/2012 |
| WO | 2012040528 A1 | 3/2012 |
| WO | 2012160157 A1 | 11/2012 |
| WO | 2014179774 A1 | 11/2014 |
| WO | 2015114158 A1 | 8/2015 |

OTHER PUBLICATIONS

Office Action dated Sep. 29, 2013 in CN Application No. 201080040968.7.

Extended European Search Report dated Jul. 3, 2017 in EP Application No. 16190054.3.

Extended European Search Report dated Mar. 8, 2016 in EP Application No. 14166592.7.

West Introduces The Daikyo Crystal Zenith RU Prefillable Syringe, Pharmaceutical Online, Jun. 2008, downloaded from webpage: http://www.pharmaceuticalonline.com/article.mvc/west-intro-duces-prefillable-syringe-system, Download date: Jan. 2009, original posting date: Jun. 2008, 2 pages.

Office Action dated May 25, 2016 in U.S. Appl. No. 14/874,017 by Cabiri.

Partial European Search Report dated Nov. 24, 2015 in EP Application No. 14166592.7.

Office Action dated Dec. 1, 2015 in CN Application No. 201410289204.1.

Int'l Preliminary Report on Patentability dated Jul. 16, 2015 in Int'l Application No. PCT/US2013/078040.

Notice of Allowance dated Aug. 24, 2015 in U.S. Appl. No. 29/479,307 by Norton.

Office Action dated Sep. 9, 2015 in U.S. Appl. No. 13/643,470 by Alon.

U.S. Appl. No. 14/850,450 by Gross, filed Sep. 10, 2015.

U.S. Appl. No. 14/880,673 by Cabiri, filed Oct. 12, 2015.

Office Action dated Sep. 30, 2015 in U.S. Appl. No. 13/667,739 by Cabiri.

Office Action dated Sep. 18, 2015 in U.S. Appl. No. 13/874,085 by Cabiri.

Office Action dated Nov. 4, 2013 in EP Application No. 11 709 234.6.

Office Action dated Dec. 17, 2013 in JP Application No. 2012-529808.

(56) References Cited

OTHER PUBLICATIONS

Office Action dated Dec. 10, 2013 in CN Application No. 201180006567.4.
Office Action dated Jan. 8, 2014 in U.S. Appl. No. 13/521,167 by Cabiri.
U.S. Appl. No. 29/479,307 by Norton, filed Jan. 14, 2014.
U.S. Appl. No. 14/193,692 by Gross, filed Feb. 28, 2014.
Office Action dated Feb. 4, 2014 in EP Application No. 11 707 942.6.
English translation of an Office Action dated Mar. 5, 2014 in CN Application No. 200880117084.X.
Int'l Search Report and Written Opinion dated Apr. 3, 2014 in Int'l Application No. PCT/US2013/078040.
Extended European Search Report dated Mar. 27, 2014 in EP Application No. 14154717.4.
Office Action dated Feb. 28, 2014 in CN Application No. 201180006571.0.
U.S. Appl. No. 14/258,661 by Cabiri, filed Apr. 22, 2014.
Int'l Search Report and Written Opinion dated Jan. 7, 2014 in Int'l Application No. PCT/US2013/065211.
Office Action dated May 23, 2014 in U.S. Appl. No. 13/472,112 by Cabiri.
Office Action dated Jun. 3, 2014 in JP Application No. 2010-527595.
Office Action dated Jul. 7, 2014 in U.S. Appl. No. 12/244,666 by Gross.
Int'l Search Report and Written Opinion dated Jul. 31, 2014 in Int'l Application No. PCT/US2014/033598.
Extended European Search Report dated Aug. 7, 2014 in EP Application No. 1417477.4.
Office Action dated Aug. 6, 2014 in EP Application No. 11 707 942.6.
Office Action dated Sep. 2, 2014 in JP Application No. 2012-550069.
Office Action dated Sep. 2, 2014 in JP Application No. 2012-550068.
Office Action dated Aug. 26, 2014 in CN Application No. 201180006567.4.
Int'l Preliminary Report on Patentability dated Oct. 9, 2014 in Int'l Application No. PCT/US2013/033118.
Office Action dated Oct. 9, 2014 in U.S. Appl. No. 13/873,335.
Office Action dated Nov. 5, 2014 in U.S. Appl. No. 13/643,470 by Alon.
U.S. Appl. No. 14/553,399 by Cabiri, filed Nov. 25, 2014.
Office Action dated Nov. 2, 2014 in CN Application No. 201180006571.0.
Office Action dated Nov. 21, 2014 in U.S. Appl. No. 13/472,112 by Cabiri.
Office Action dated Nov. 27, 2014 in U.S. Appl. No. 13/429,840 by Cabiri.
Int'l Preliminary Report on Patentability dated Nov. 27, 2014 in Int'l Application No. PCT/US2013/039465.
U.S. Appl. No. 14/593,051 by Gross, filed Jan. 9, 2015.
U.S. Appl. No. 14/683,193 by Cabiri, filed Apr. 10, 2015.
Office Action dated Feb. 20, 2015 in U.S. Appl. No. 13/521,181 by Cabiri.
Office Action dated Feb. 24, 2015 in U.S. Appl. No. 14/258,661 by Cabiri.
U.S. Appl. No. 14/638,525 by Filman, filed Mar. 4, 2015.
Extended European Search Report dated Feb. 23, 2015 in EP Application No. 14166596.8.
Office Action dated Mar. 10, 2015 in U.S. Appl. No. 13/643,470 by Alon.
Office Action dated Mar. 10, 2015 in U.S. Appl. No. 12/244,666 by Gross.
Extended European Search Report dated Feb. 23, 2015 in EP Application No. 14166591.9.
Office Action dated Mar. 10, 2015 in CN Application No. 201180006567.4.
Office Action dated Mar. 31, 2015 in JP Application No. 2012-550068.
Int'l Preliminary Report on Patentability dated May 14, 2015 in Int'l Application No. PCT/US2013/065211.
Office Action dated May 7, 2015 in JP Application No. 2012-550069.
Office Action dated May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action dated May 1, 2015 in U.S. Appl. No. 14/638,525 by Filman.
Office Action dated Jun. 4, 2015 in U.S. Appl. No. 13/667,739 by Cabiri.
Office Action dated Jul. 31, 2015 in U.S. Appl. No. 13/521,181 by Cabiri.
Office Action dated Aug. 13, 2015 in U.S. Appl. No. 14/553,399 by Cabiri.
Office Action dated Jan. 8, 2013 in JP Application No. 2010-527595.
Office Action dated Nov. 5, 2013 in JP Application No. 2010-527595.
Daikyo Crystal Zenith® polymer, Manufactured by Daikyo Seiko, Ltd. (Jun. 25, 2008).
Copaxone®, Manufactured by Teva Pharmaceutical Industries Ltd. (2009).
Int'l Search Report dated May 13, 2009 in Int'l Application No. PCT/IL2008/001312.
Int'l Preliminary Report on Patentability dated Apr. 7, 2010 in Int'l Application No. PCT/IL2008/001312; Written Opinion.
Int'l Search Report dated Apr. 26, 2010 in Int'l Application No. PCT/US2009/069552.
Office Action dated Apr. 5, 2010 in U.S. Appl. No. 12/244,666.
Office Action dated Sep. 21, 2010 in U.S. Appl. No. 12/244,666.
Office Action dated Apr. 5, 2010 in U.S. Appl. No. 12/244,688.
Office Action dated Sep. 2, 2010 in U.S. Appl. No. 12/244,688.
Office Action dated Sep. 30, 2010 in U.S. Appl. No. 12/689,250.
Int'l Search Report dated Jan. 12, 2011 in Int'l Application No. PCT/US2010/048556; Written Opinion.
U.S. Appl. No. 60/997,459, filed Oct. 2, 2007.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
International Preliminary Report on Patentability dated Jul. 5, 2011 in International Application No. PCT/US2009/069552; Written Opinion.
Office Action dated Jul. 13, 2011 in U.S. Appl. No. 12/559,563.
Int'l Preliminary Report on Patentability dated Sep. 1, 2011 in Int'l Application No. PCT/US2010/048556.
Office Action dated Sep. 6, 2011 in U.S. Appl. No. 12/345,818.
Office Action dated Feb. 21, 2012 in U.S. Appl. No. 12/689,249.
Int'l Search Report dated Jun. 17, 2011 in Int'l Application No. PCT/US2011/021604.
Int'l Search Report dated Oct. 12, 2011 in Int'l Application No. PCT/US2011/021605.
Office Action dated Oct. 28, 2011 in U.S. Appl. No. 12/615,828.
Int'l Search Report dated Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action dated May 16, 2012 in U.S. Appl. No. 12/615,828.
Office Action dated Jul. 2, 2012 in U.S. Appl. No. 13/272,555.
Office Action dated May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability dated Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
Office Action issued Jan. 8, 2013 in JP Application No. 2010-527595.
Int'l Preliminary Report on Patentability dated Feb. 7, 2013 in Int'l Application No. PCT/US2011/021604.

(56) References Cited

OTHER PUBLICATIONS

Int'l Preliminary Report on Patentability dated Feb. 7, 2013 in Int'l Application No. PCT/US2011/021605.
English translation of an Office Action dated Jan. 30, 2013 in CN Application No. 200880117084.X.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
Int'l Search Report and Written Opinion dated Jul. 26, 2013 in Int'l Application No. PCT/US2012/039465.
Int'l Search Report and Written Opinion dated Aug. 5, 2013 in Int'l Application No. PCT/US2013/033118.
U.S. Appl. No. 13/964,651 by Gross, filed Aug. 12, 2013.
Office Action dated Aug. 15, 2013 in CN Application No. 200880117084.X.
Office Action dated Oct. 9, 2013 in IL Application No. 208634.
Office Action dated Dec. 15, 2017 in U.S. Appl. No. 15/269,248, by Cabiri.

\* cited by examiner

ROTATION RESISTANT FRICTION ADAPTER FOR PLUNGER DRIVER OF DRUG DELIVERY DEVICE

FIELD AND BACKGROUND OF THE INVENTION

The present invention, in some embodiments thereof, relates to an anti-rotational friction fitting, more particularly, but not exclusively, to a fitting for preventing rotation of a plunger driver of a drug delivery device.

U.S. Pat. No. 7,967,795 to the present inventor (Oz Cabiri) discloses "a cartridge interface assembly including a driving plunger including an outer shaft, and a driver including an inner shaft, the inner shaft mating with an intermediate shaft, the intermediate shaft mating with the outer shaft, so that the shafts are movable telescopically with respect to one another, wherein rotation of the driver causes the driving plunger to advance in a direction away from the driver".

SUMMARY OF THE INVENTION

According to an aspect of some embodiments of the invention, there is provided an assembly for driving a plunger and in a drug reservoir, the plunger dividing between a drug in a distal portion of the reservoir and a proximal opening of the reservoir; the assembly comprising: a telescoping shaft that extends by rotation of a driving element in a first rotational direction with respect to a distal shaft; a distal end of the distal shaft configured to engage the plunger; and a radial element extending from the distal shaft to contact an interior side wall of the reservoir, the element configured and oriented to wedge between the interior wall and the distal shaft when the distal shaft is rotated in the first rotational direction.

According to some embodiments of the invention, the element includes a virtual sprag having a long axis and wherein the long axis intersects the interior side wall.

According to some embodiments of the invention, the long axis intersects the interior side wall at an angle between 91 and 120 degrees from the first rotational direction.

According to some embodiments of the invention, the element includes a virtual beam having a preferred bending direction opposite the first rotational direction.

According to some embodiments of the invention, the assembly further comprises: a plunger interface configured to engage the plunger; the plunger interface irrotationally interconnecting the distal shaft and the plunger when the plunger interface is engaged to the plunger.

According to some embodiments of the invention, the assembly further comprises: a vent for releasing gas from a space between the element and the plunger.

According to some embodiments of the invention, the radial element is located proximal to the distal end of the distal shaft.

According to some embodiments of the invention, the wedging is longitudinal such that moving the distal shaft distally with respect to the reservoir reduces a normal force between the radial element and the interior wall.

According to some embodiments of the invention, a resistance due to friction between the radial element and the interior wall to movement of the distal shaft in the first rotational direction is higher resistance due to friction between the radial element and the interior wall to movement of the distal shaft in a direction opposite the first rotational direction.

According to some embodiments of the invention, the assembly further comprises: a second friction element extending from a drug delivery device to contact an exterior side wall of the reservoir when the reservoir is inserted into the drug delivery device, the second friction element is configured and oriented to wedge between the exterior wall and the reservoir when the reservoir is rotated in a second rotational direction.

According to some embodiments of the invention, the second rotational direction is opposite the first rotational direction.

According to an aspect of some embodiments of the invention, there is provided a method of advancing a plunger in a drug reservoir comprising: providing a telescoping assembly that extends by rotating a driver in a first direction with respect to a pushing shaft mated to the driver, the pushing shaft including a friction element in contact with a wall of the reservoir; rotating the driver in the first direction; wedging the friction element between the pushing shaft and the wall as result of the rotating; inhibiting rotation of the first direction as a result of the wedging; and unwedging the friction element to facilitating advancing of the pushing shaft.

According to some embodiments of the invention, the wedging is substantially the only process impeding rotation of the pushing shaft with respect to the reservoir.

According to some embodiments of the invention, wedging include increasing normal force.

According to some embodiments of the invention, the method further comprises: reducing a normal force between the friction element and the wall of the reservoir when the pushing shaft moves in a distal direction.

According to some embodiments of the invention, the drug reservoir includes a plunger, the method further comprising: reducing a normal force between the friction element and the wall of the reservoir when the pushing shaft pushes distally against the plunger.

According to an aspect of some embodiments of the invention, there is provided a drug delivery device comprising: a housing including a channel; a drug reservoir fitting into the channel; and a friction element extending from a housing to the channel to contact an exterior side wall of the reservoir when the reservoir is inserted into the channel, the element configured and oriented to wedge between the exterior wall and the reservoir when the reservoir is rotated in a first rotational direction.

According to some embodiments of the invention, the assembly further comprises: a telescoping shaft that extends by rotation of a driving element in a first rotational direction with respect to a shaft; and a second friction element inhibiting rotation of the shaft with respect to the reservoir.

According to some embodiments of the invention, the channel is cylindrical and includes an opening at one end and wherein the reservoir slides longitudinally through the opening into the channel and wherein the friction element has increased friction resistance to movement in the first rotational direction than to movement in the longitudinal direction.

According to an aspect of some embodiments of the invention, there is provided a method of distributing a drug comprising: supplying a reservoir containing the drug and a distribution device including a channel and a friction element; inserting the reservoir into longitudinally into the channel; and wedging the reservoir against the friction element by rotating the reservoir with respect to the device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Overview

Figure 1:
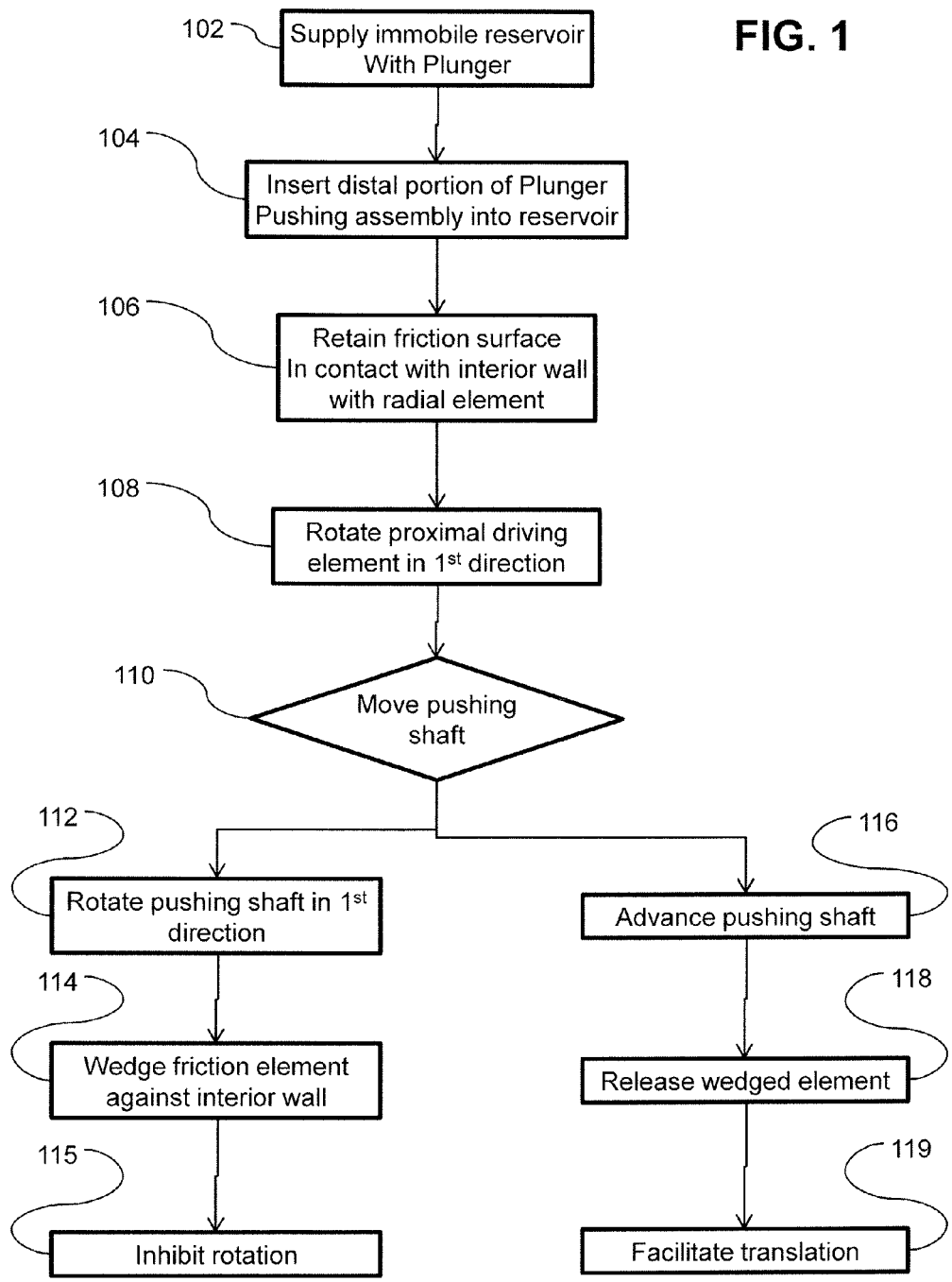
FIG. 1 is a flow chart illustration of a method of facilitating movement of a plunger driver in accordance with embodiments of the current invention.

The present invention, in some embodiments thereof, relates to an anti-rotational friction fitting, more particularly, but not exclusively, to a fitting for preventing rotation of a plunger driver and/or a reservoir of a drug delivery device.

An aspect of some embodiments of the present invention relates to a variable friction element facilitating forward movement of a plunger pushing shaft inside a drug reservoir. For example, forward motion of the pushing shaft may be driven by rotation of a driver element with respect to the pushing shaft. The friction element may facilitating the relative rotation for example by inhibiting the pushing shaft from rotating along with the driving element and/or by inhibiting rotation of the reservoir. Alternatively or additionally, the friction element may be designed to reduce friction to forward movement of the pushing shaft and/or reservoir (facilitating movement in the forward, preferred direction).

In some embodiments, the friction element may facilitate and/or speed up forward movement of the pushing shaft and/or plunger interface prior to contact with the plunger. Optionally, when the pushing shaft is pushing the plunger, resistance to forward movement due to the friction element may be reduced and/or may self-adjust to minimal and/or may be negligible.

As used herein the term plunger means a piston element. For example, a plunger may include a plunger shaft and/or a plunger head and/or a plunger seal and/or a mating element. As used herein, the term/phrase plunger seal means a piston element that impedes fluid flow. Optionally, plunger seal includes and/or is integral to a piston head. For example, the seal may have the form of a stopper and/or a gasket. In some embodiments, the term plunger may refer to the plunger seal alone. For example, the plunger may include a single sealing element that is pushed by a driver. Optionally, the driver may include a pushing shaft.

In some embodiments, the friction element is configured to wedge and/or increase a normal force between an outer wall of the shaft and an inner wall of the reservoir when the shaft moves in an inhibited direction with respect to the reservoir. In some embodiments, the friction element is configured to wedge and/or increase a normal force between an outer wall of the reservoir and a drug delivery device when the reservoir moves in an inhibited direction with respect to the delivery device. Alternatively or additionally, the friction element is configured to become dislodged and/or reduce a normal force between an outer wall of the shaft and in inner wall of the reservoir when said shaft moves in a preferred direction with respect to the reservoir. In some embodiments, the preferred direction of movement is in a direction that causes the rod to approach the plunger and/or discharge the drug, for example advancement, for example in the distal direction.

In some embodiments, the friction element may include a sprag and/or a beam. For example, a beam may have a preferential mode of bending that causes anisotropic friction. Optionally, the sprag and/or beam may include a separate element. Alternatively or additionally, the sprag and/or beam may be integral to another element and/or other elements. As used herein the term virtual element (for example virtual sprag and/or virtual beam) means an element that is intrinsic to another element. For example, a virtual sprag and/or beam may be a region of a radial element (for example the radial element may include a disk) having decreased compressibility in comparison to a surrounding region. For example, a virtual sprag and/or beam may include a rib on a radial element.

In some embodiments, a sprag may be an element that is propped between two surfaces at an angle such that a movement of one of the surfaces in first direction compresses the sprag and/or wedges the sprag between the two surfaces thereby increasing a normal force and/or a resistance to the movement. Alternatively or additionally, movement of the surface in a direction different from the first direction may reduce a normal force and/or decrease resistance to the movement and/or reducing resistance to another movement. A virtual and/or a combined sprag may include a portion of an element having properties that cause variable friction between two surface such that a movement in first direction compresses the sprag increasing resistance to the movement and/or a movement in a direction different from the first direction releases a force on the sprag decreasing resistance to the opposite movement and/or to any movement. For example, frictional resistance to movement in the inhibited direction may range between 2× to 4× as large and/or between 4× to 10× and/or between 10× to 100× or greater than 100× as great as frictional resistance to movement in an another direction (for example an opposite direction from the first direction) and/or as frictional resistance to movement in the preferred direction. For example, movement in the preferred direction may reduce frictional resistance to movement by 2× to 4× and/or by 4× to 10× and/or by 10× to 100× or greater than 100×. The combination of increasing frictional resistance to movement in a non-preferred direction while reducing frictional resistance to movement in a preferred direction may reduce and/or minimize friction resistance to movement in the preferred direction while increasing and/or maximizing resistance to other movements.

In some embodiments, a friction fitting and/or a plunger interface may include an air vent. The air vent may prevent buildup of an air pocket between the plunger interface and the plunger as the pushing shaft and/or plunger interface approaches the plunger.

In some embodiments, the friction element of the present invention may work with various forms of medicine reservoirs and/or plungers. For example, the invention may be configured for a standard syringe, cartridge, reservoir and/or plunger. For example, the cavity of the reservoir may be cylindrical. For example, the cavity of the reservoir may have smooth walls.

An aspect of some embodiments of the present invention relates to an element that produces high friction when the pushing shaft is moving with minimal external resistance and/or produces reduced friction when the pushing shaft is pushing against a plunger of the reservoir. For example, the plunger interface may be configured to cause the friction element to fold and/or bend away from the walls of the reservoir and/or reduce friction when the interface engages the plunger.

In some embodiments, the plunger interface may include a standard connector. For example, the plunger interface may include a screw that screws into the plunger. The interface may transfer linear force and/or rotational torque between the pushing shaft and the plunger. Alternatively or additionally, the interface may transfer linear force in one or more directions while transferring limited and/or negligible torque between the pushing shaft and the plunger. For example, a plunger interface may include a screw thread. Until the screw interface reaches the plunger, the friction element may inhibit rotation and/or facilitate linear movement of the pushing shaft. As the screw element engages between the pushing shaft and the plunger, resistance is optionally added against forward motion of the pushing shaft and/or the friction inhibiting rotation of the pushing shaft is optionally reduced. Optionally, the interface and/or the pushing shaft will rotate, engaging the screw threads. At some point of engagement of the screw threads (for example when they are fully screwed together and/or fully engaged), the resistance of the plunger to rotation will optionally stop and/or reduce rotation of the pushing shaft and/or facilitate further linear advance of the plunger and/or pushing shaft. Alternatively or additionally, a plunger interface may include a locking element, for example a plug and socket that transfers torque and/or linear force between the pushing shaft and the plunger. Alternatively or additionally, the plunger may include a ram interface with pushes the plunger without transferring significant rotational torque.

In some embodiments, a friction element may be adjusted according the drive system, injection schedule and/or load on the plunger. For example, for a high viscosity payload where the load on the injector is high, the friction element may be designed with lower friction resistance to forward movement. For example, where injection is fast (e.g. for a for a high pitch driving screw) the friction element may be designed with lower friction resistance to forward movement. For example, for a reservoir having approximately 100 g*cm of torque generated pushing the drug during delivery, a friction element may have a torque resistance in an non-preferred direction of approximately 90 g*cm and/or a plunger may have a torque resistance of approximately 60 g*cm such that the combined torque resistance in the non-preferred direction of the friction element and plunger may be approximately 150 g*cm. More generally, the torque resistance of the friction element in a non-preferred direction may range between 80 to 95% and/or between 65 to 80% and/or between 30 to 65% and/or between 5 to 30% and/or between 95 to 110% and/or between 110 to 175% and/or between 175 to 300% the torque generated by discharging the drug during delivery. The combined torque resistance in a non-preferred direction of the friction element and the plunger may range for example between 105% to 130% and/or 130% to 170% and/or between 170% to 250% and/or 250% to 500% the torque generated by discharging the drug during delivery. The torque generated discharging the drug during delivery may depend for example on the internal bore of an injection needle and/or on the cross sectional area of the reservoir and/or on the viscosity of the medicine and/or on a pitch of a driving screw. For example, for a 8.65 inner diameter reservoir with a 27G ultra thin wall delivery needle and a drug with viscosity between 30 to 50 cp, and an axial plunger speed of 1-3 cm/min, the axial force discharging the drug may be for example in the range between 0.2-3 kgf, the delivery torque discharging the drug during may range for example between 50-150 gr*cm torque on the screw. The combined torque resistance in a non-preferred direction of the friction element and the plunger may range for example between 50 to 300*gr·cm. For example as viscosity, the screw pitch, the cross sectional area increase and/or as the needle bore diameter decreases, the delivery torque may increase. Table 1 shows some approximate exemplary values for delivery torque (for example with an 8.65 inner diameter reservoir with a 27G ultra thin wall delivery needle). For example, the delivery torque discharging the drug during may range between 30 to 45 g*cm and/or between 45 to 70 g*cm and/or between 70 to 90 g*cm and/or between 90 to 130 g*cm and/or between 130 to 200 g*cm and/or between 200 to 1000 g*cm.

TABLE 1 examples of delivery torque for discharging the drug
(not including friction of the friction element and the
plunger with the wall of the reservoir)
Torque Generated While Delivery

| | Viscosity of Drug | | |
|---|---|---|---|
| TSA pich | 1 cp | 30 cp | 60 cp |
| 0.75 mm | 49.4 g * cm | 74 g * cm | 123 g * cm |
| 0.85 mm | 51 g * cm | 86.5 g * cm | 127 g * cm |
| 1 mm | 53 g * cm | 86 g * cm | 133 g * cm |

In some embodiments, tradeoffs are possible. For example, for a higher viscosity drug, a lower pitch driving screw may be used and/or a higher friction anti-rotational pad may be used with a high pitch screw and/or a larger bore needle may be used. For example, the pitch of a driving screw may range between 3 mm to 1 mm and/or between 1 mm to 0.8 mm and/or between 0.8 mm to 0.6 mm and/or between 0.6 mm to 0.3 mm and/or between 0.3 mm to 0.2 mm.

In some embodiments, the friction element may be configured to reduce frictional resistance to axial advance of the pushing shaft. For example, the normal force between the friction element and the wall of the reservoir may be increased by tangential movement and/or decreased by axial movement. For example, the ratio of normal force during tangential movement to normal force during axial movement may range between 1.1 to 4 and/or between 4 to 10 and/or between 10 to 100 and/or more than 100. In some embodiments, the ratio of friction coefficient during tangential movement to the friction coefficient during axial movement may range between 1.1 to 4 and/or between 4 to 10 and/or between 10 to 100 and/or greater than 100.

In some embodiments, a friction element may include a directional friction surface, for example micro nails and/or an embossed surface pattern and/or slanted hairs and/or scales and/or a non-isotropic molecular structure etc.

In some embodiments, after advancing in and unengaged state, the shaft may be engaged to a plunger.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Facilitating Preferred Movement of a Plunger Driver

FIG. 1 is a flow chart illustration of a method of facilitating movement of a plunger pushing shaft in accordance with embodiments of the current invention. In some embodiments, a friction element may, for example, prevent the pushing shaft from rotating with respect to a reservoir thereby facilitating relative rotation between the pushing shaft and a driver element. Optionally, whenever the pushing shaft begins to rotate in an inhibited direction, friction between the pushing shaft and the reservoir increases. In some embodiments, friction is reduced when the pushing shaft advances. For example, reduction in friction may reduce a load on a drive system while pushing the plunger and/or discharging a drug.

In some embodiments, an immobile medicine reservoir may be supplied 102. For example, the reservoir may have a cylindrical cavity with a distal opening and/or a proximal opening. A plunger is optionally inserted in the cylindrical cavity. For example, the plunger may divide between a distal portion of the cavity containing the drug and the proximal portion of the cavity.

In some embodiments, a distal portion of a telescoping plunger pushing assembly may be inserted 104 into the proximal opening of the reservoir. For example, the distal portion of a telescoping plunger pushing assembly may include a pushing shaft and/or a distal portion thereof, a plunger interface and/or a friction element. Optionally a plunger interface of the pushing assembly will engage the plunger when the assembly is inserted 104. Alternatively or additionally, the plunger interface may remain disengaged from the plunger when the assembly is inserted 104 into the reservoir. In some embodiments, the distal end of the pushing assembly may be inserted 104 until it contacts the plunger. Alternatively or additionally, after insertion 104, the distal end of the pushing assembly may remain distanced proximally from the plunger.

In some embodiments, a friction surface may be retained 106 in contact with an interior wall of the reservoir and/or with the pushing shaft. For example, when the system is at rest, a radial element may keep at least a minimal normal force between the friction surface and the interior wall of the reservoir. For example, the radial element may be flexible and/or elastically compressible.

In some embodiments, a driving element may be rotated 108 in a first direction. Optionally the driving element may be engaged to the pushing shaft. For example, rotation 108 of the driving element may cause the pushing shaft to move 110. For example, the pushing shaft may tend to rotate 112 along with the driving element in the first direction. In some embodiments in may be desired to inhibit rotation 112 of the pushing shaft. For example, when telescoping is driven by relative rotation between the driving element and the pushing shaft, rotation 112 of the pushing shaft along with the driving element may be undesirable. Optionally, the friction element may be configured such that rotation 112 of the pushing shaft in the first direction wedges 114 the friction element and/or the radial element between the pushing shaft and the walls of the reservoir. Wedging 114 of the friction element between the driving shaft and the non-rotating reservoir optionally increases a normal force between the friction element and the walls of the reservoir and/or increases friction between the driving shaft and the reservoir and/or inhibits 115 rotation 112 of the pushing shaft.

In some embodiments, a set of screw threads may engage between the driver element and the pushing shaft. For example, rotation 108 of the driver element in the first direction with respect to the pushing shaft may advance 116 the pushing shaft distally into the reservoir. For example, advancing 116 may cause the pushing shaft to approach the plunger and/or cause the interface to engage the plunger and/or cause the plunger to advance distally. Optionally, the friction element and/or the radial element is configured such that advancing 116 the pushing shaft releases 118 a wedged element, for example the friction element and/or the radial element. Releasing 118 the wedged element optionally decreases a normal force between the friction element and the walls of the reservoir and/or decreases friction between the driving shaft and the reservoir and/or facilitates 119 advancing of the pushing shaft.

Figure 2:
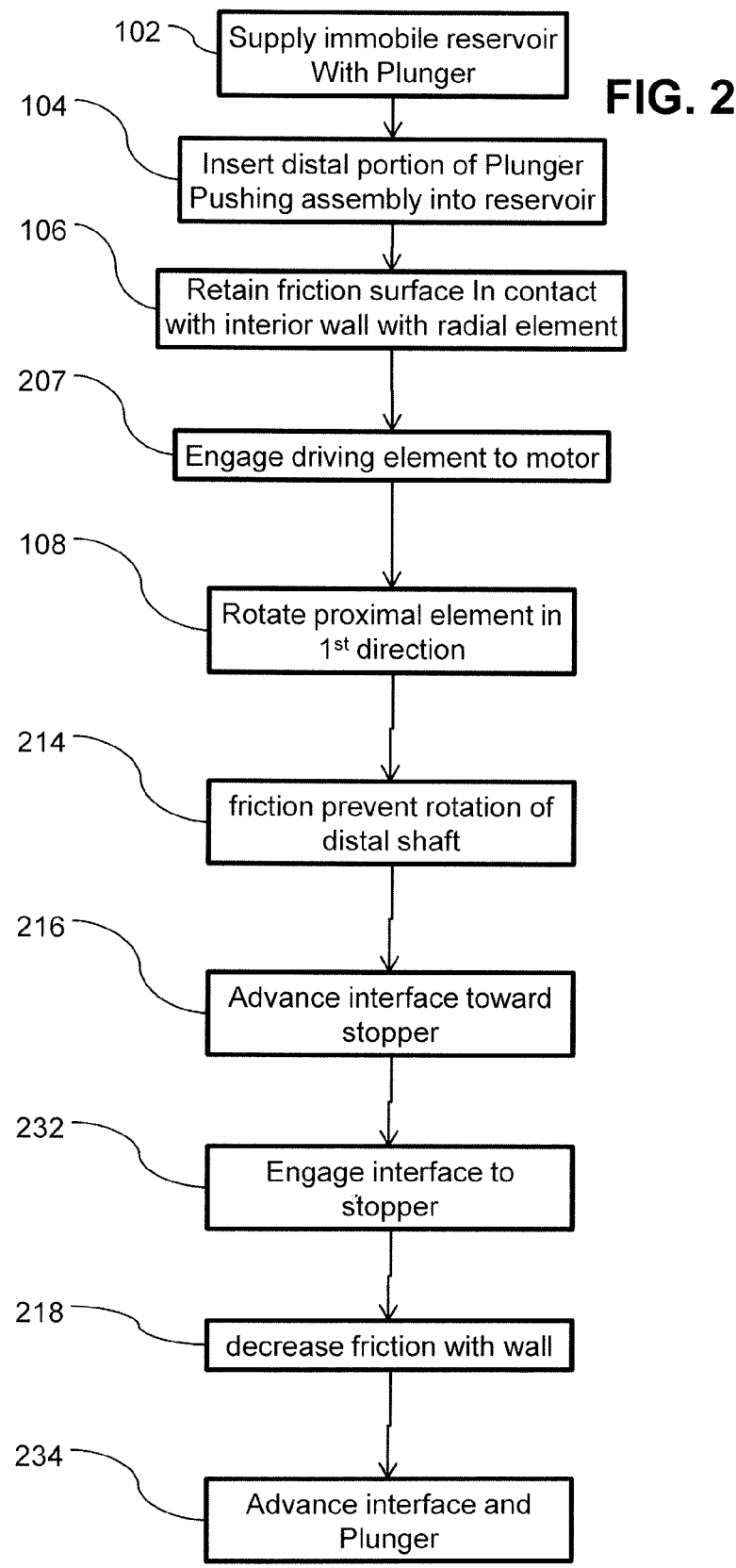
FIG. 2 is a flow chart illustration of a method of driving a plunger in accordance with embodiments of the current invention.

FIG. 2 is a flow chart illustration of a method of driving a plunger in accordance with embodiments of the current invention. Optionally, the plunger is driven by an advancing pushing shaft. For example, advancing of the pushing shaft may be motivated by relative rotation of a drive element with respect to a pushing shaft. Tangential friction between a friction element and the reservoir may supply counter rotational torque between the pushing shaft and the reservoir, facilitating relative rotation between the pushing shaft and the driver element. In some embodiments, the pushing shaft may advance in the reservoir while the pushing shaft is unengaged to the plunger. Optionally, while the pushing shaft and the plunger are unengaged, the tangential friction between the friction element and the reservoir may be substantially the only force preventing the pushing shaft from rotating along with the rotating element. In some embodiments, the friction element may be configured to produce increased resistance to an undesired movement (for example rotation with the driving element) and/or decreased resistance to a desired movement (for example advancing of the plunger).

In some embodiments, a distal portion of a plunger pushing assembly may be inserted 104 into a proximal opening of a drug reservoir. Optionally, the drug reservoir is rotationally immobile. Optionally, the drug reservoir includes a plunger separating between a drug in a distal portion of the reservoir and the proximal opening of the reservoir. Optionally, after insertion, a plunger interface of the pushing assembly may remain distanced proximally from the plunger. Optionally, the plunger interface is mounted on a distal portion of the pushing shaft.

In some embodiments, after the distal end of the plunger driving assembly is inserted 104 into the reservoir, a driving element may be engaged 207 to a power source. Alternatively or additionally, the driving element may be engaged 207 to the power source before being insertion 104 of the pushing assembly. For example, the power source may include an electric motor. The power source optionally rotates 108 the driving element in a first direction.

In some embodiments, during rotation 108 of the driving element in the first direction; the pushing shaft may be inhibited 214 from rotating by friction between a friction element and the inner wall of the reservoir. Optionally, rotation 108 of the driving element in the first direction relation to a pushing shaft causes the pushing shaft to telescope and/or move distally with respect to the driving element. For example, the pushing shaft and/or the plunger interface may be advanced 216 distally until it reaches the plunger.

In some embodiments, the plunger interface may engage 232 the plunger. For example, the plunger interface may transfer axial force between the plunger and the pushing shaft. In some embodiments, the plunger interface may limit rotation between the plunger and the pushing shaft. For example, after engagement of the plunger, friction between the plunger and the interior wall of the reservoir may prevent rotation of the pushing shaft in addition to and/or in place of the friction element. Alternatively or additionally, the plunger interface may allow rotation of the pushing shaft with respect to the plunger. Optionally, allowing rotation of the pushing shaft with respect to the plunger may reduce rotational stresses on the plunger.

In some embodiments, when the pushing shaft is advancing and/or when the plunger interface is engaged to the plunger, friction between the friction element and the wall of the reservoir may be reduced 218. Reducing the friction may make it easier to advance 216 the plunger driver and/or advance 234 the plunger.

Block Diagram of an Anti-Rotation System

Figure 3A:
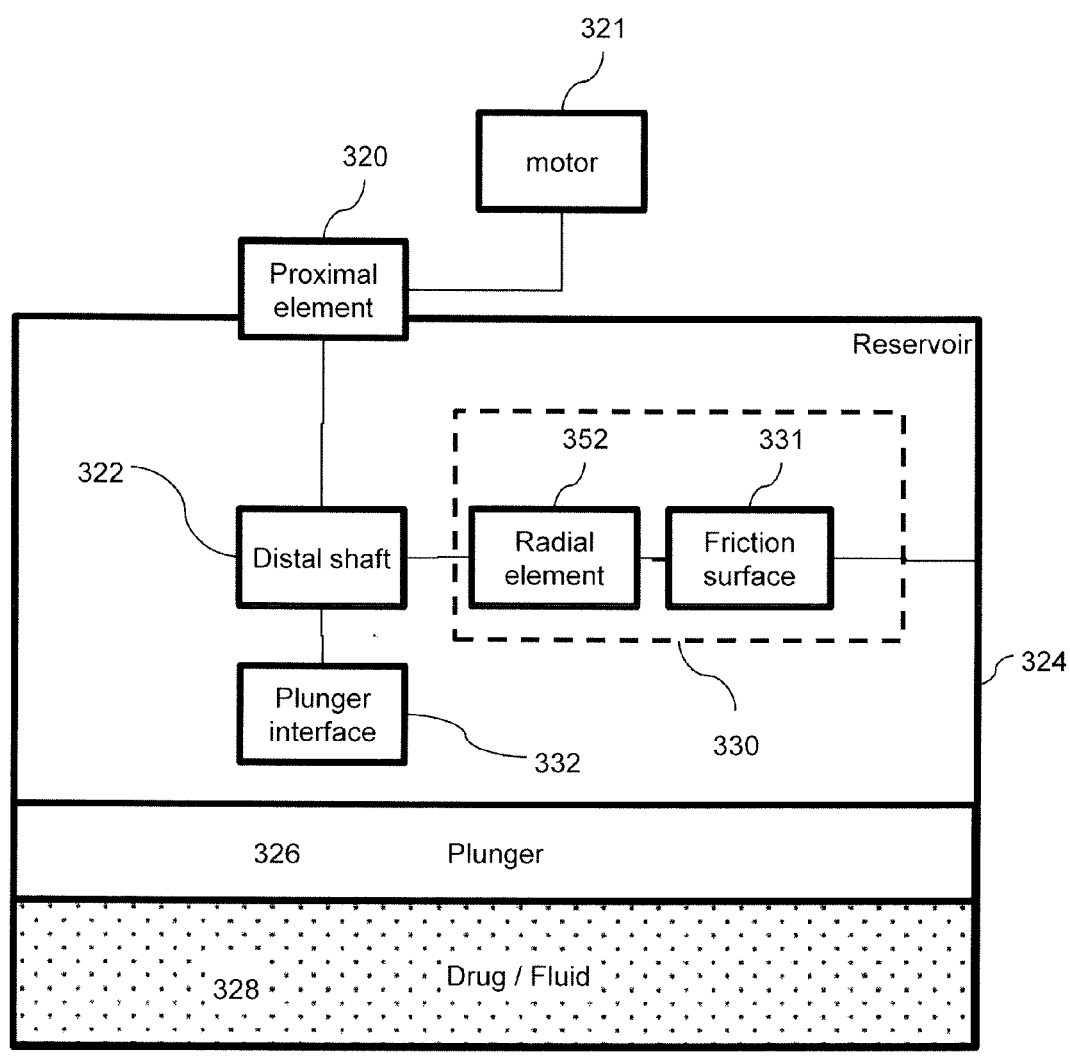
FIG. 3A is a block diagram illustration of an assembly for driving a plunger in accordance with embodiments of the current invention.

FIG. 3A is a block diagram illustration of a drug reservoir and an assembly for driving a plunger in accordance with embodiments of the current invention. For example, plunger driving assembly may include a variable friction assembly 330 and/or a telescoping assembly including a proximal element 320 and/or a distal shaft 322 and/or a plunger interface 332. The telescoping assembly optionally telescopes via rotation of proximal element 320 (for example a driver element) with respect to distal shaft 322 (for example a plunger pushing shaft). For example, proximal element 320 may be rotated with respect to a drug reservoir 324 and/or distal element 322 is hindered from rotating with respect to drug reservoir 324. Optionally, distal element 322 is hindered from rotation by friction with the walls of reservoir 324. For example, friction with the walls of drug reservoir 324 may be supplied by variable friction assembly 330. For example, variable friction assembly 330 may have high resistance to rotation and/or tangential movement with respect to the drug reservoir and/or low resistance to axial translation with respect to the drug reservoir. Optionally, a motor 321 rotates proximal element 320 with respect to reservoir.

In some embodiments, variable friction assembly 330 may include a radial element 352 and/or a friction surface 331. Optionally, radial element 352 links friction surface 331 to distal shaft 322. Optionally, radial element 352 retains friction surface 331 in contact with an interior wall of reservoir 324.

In some embodiments, radial element 352 maintains a variable normal force between friction surface 331 and the interior wall of reservoir 324. For example, radial element 352 may be wedged between the interior wall of reservoir 324 and shaft 322 such that tangential movement of friction surface 331 in at least one direction causes compression of radial element (optionally increasing the normal force). Alternatively or additionally, radial element 352 may be wedged between the interior wall of reservoir 324 and shaft 322 such that axial movement of friction surface 331 in the distal direction causes release of compression of radial element (optionally decreasing the normal force). For example, the radial element may include one or more of a sprag, a virtual sprag, a beam having a preferred bending direction, a clutch dog, a wedge, a prop and/or a virtual beam having a preferred bending direction.

In some embodiments, radial element 352 may be wedged by movement in any of a plurality of directions. For example, radial element 352 may include a trapezoidal sprag that is wedged on one side by movement in one direction and on the other side by movement in an opposite direction. Alternatively or additionally, friction assembly 330 may include multiple anisotropic sprags and/or beams oriented in different directions to cause increased friction in more than one direction. For example, friction assembly 330 may have increased friction resistance to rotation around an axis in both rotational directions and/or have decreased friction to linear movement in one or more directions.

In some embodiments, friction surface 331 may have an anisotropic friction coefficient. For example, the friction coefficient may be high in one of the tangential directions optionally causing high friction resistance to rotation of the distal pushing shaft with respect to the reservoir in at least one direction and/or low friction resistance to movement distally with respect to the drug reservoir. Alternatively or additionally, the friction surface may have an isotropic coefficient of friction.

In some embodiments, proximal element 320 may be proximal to, partially inserted into and/or fully inserted into a proximal opening reservoir 324. In some embodiments, distal shaft 322 may be proximal to, partially inserted into and/or fully inserted into a proximal opening reservoir 324.

In some embodiments, reservoir 324 may contain a fluid, for example a drug 328. For example, drug 328 may be located in distal portion of reservoir 324. Optionally a plunger seal 326 may seal off and/or separate between drug 328 and the proximal opening of the reservoir and/or the plunger pushing assembly.

In some embodiments, when plunger interface 332 is engaged to plunger seal 326 it may supply a one-way, two-way or multi-dimensional connection between pushing shaft 322 and plunger seal 326. For example, plunger interface 332 may include a ram that supplies compression force between shaft 322 and plunger seal 326 for pushing plunger distally, but supplies small and/or negligible tensile force for pulling plunger seal 326 proximally. This ram may have friction surface with the plunger and/or partially intrude into the plunger. Alternatively, plunger interface 332 may include a snap, screw and/or interference element that supplies compression force between shaft 322 and plunger seal 326 for pushing plunger distally and also supplies tensile force for pulling plunger seal 326 proximally. In some embodiments, interface 332 transmits torque between plunger seal 326 and shaft 322. Alternatively or additionally, interface 332 may not transmit significant torque; for example interface 332 may include a pivot that allows shaft 322 to rotate independently of plunger seal 326.

Figure 3B:
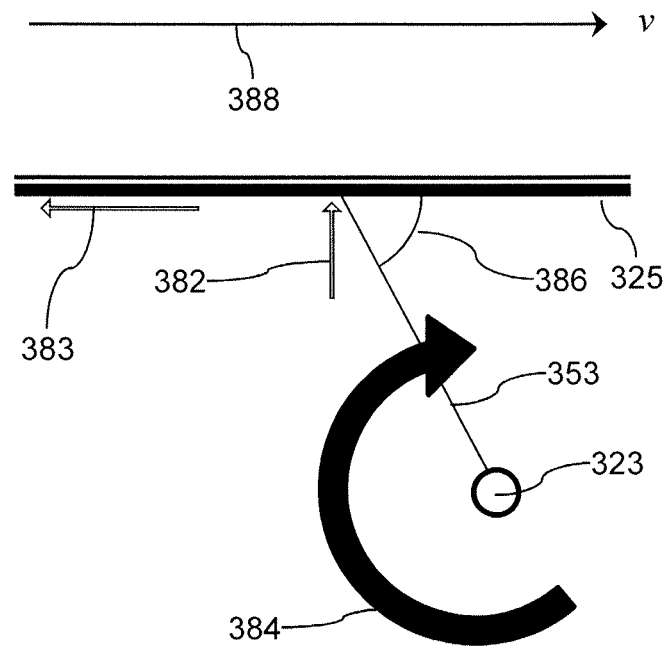
FIGS. 3B-3C are schematic diagrams of a sprag element resisting movement in a hindered direction and allowing movement in a direction other than the hindered direction in accordance with embodiments of the current invention.

FIG. 3B is a schematic diagram of a sprag 353 in accordance with an embodiment of the current invention. For example, in FIGS. 3B and 3C, sprag 353 is in contact with a surface 325. For example, in FIG. 3B surface 325 is moving in an inhibited direction indicated by arrow 388. Optionally, when surface 325 is moving in an inhibited direction, the angle of attack 386 between sprag 353 and the direction of movement will be less than 90 degrees. For example, the angle of attack may range between 89 to 85 degrees and/or between 85 to 70 degrees and/or between 70 to 45 degrees and/or between 45 to 0 degrees. Optionally, in some embodiments, a sprag may be anisotropic. For example, an angle of attach may differ on a leading and/or trailing edge. The movement of surface 325 optionally causes a rotational moment 384 on sprag 353 and/or wedges sprag 353 between the outer wall of a shaft 323 and surface 325. When movement is in the inhibited direction, rotational moment 384 and/or wedging optionally produces an increase 382 in the normal force of sprag 353 against surface 325. In some embodiments, when movement is in the inhibited direction, rotational moment 384 and/or wedging may produce an increase a force 383 of friction of sprag 353 against surface 325.

Figure 3C:
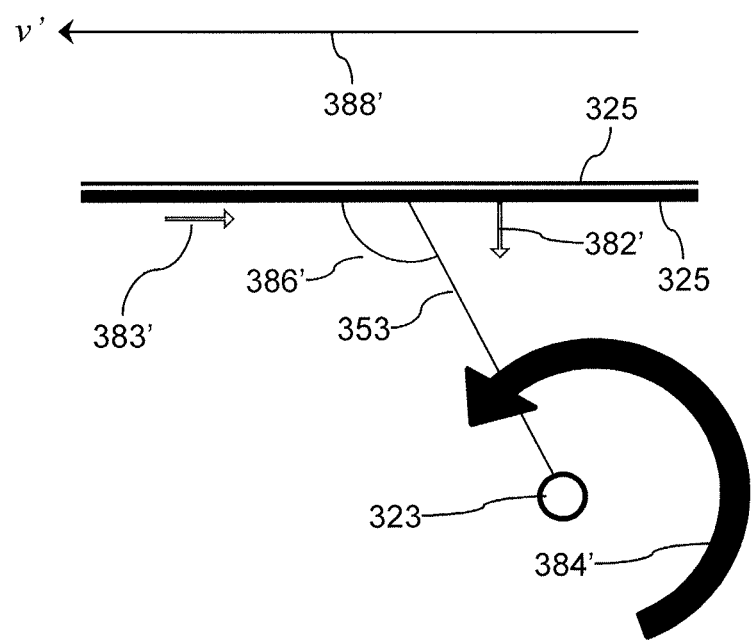

FIG. 3C is a schematic diagram of a sprag 353 in accordance with an embodiment of the current invention. For example, in FIG. 3C surface 325 is moving opposite an inhibited direction as indicated by arrow 388'. Optionally, when surface 325 is moving opposite an inhibited direction, the angle of attack 386' between sprag 353 and the direction of movement will be greater than 90 degrees. For example, the angle of attack may range between 91 to 95 degrees and/or between 95 to 120 degrees and/or between 120 to 135 degrees and/or between 135 to 180 degrees. The movement of surface 325 optionally causes a rotational moment 384' on sprag 353 and/or releases wedging of sprag 353 between the outer wall of a shaft 323 and surface 325. When movement is opposite the inhibited direction, rotational moment 384' and/or releasing the wedging optionally produces a decrease 382' in the normal force of sprag 353 against surface 325. In some embodiments, when movement is opposite the inhibited direction, rotational moment 384' and/or releasing the wedging may produce a decrease in a force 383' of friction of sprag 353 against surface 325.

Independent Anti-Rotation Sprags

FIGS. 4A-4F are drawings of a plunger driving assembly and drug reservoir with a screw-in plunger interface in accordance with embodiments of the current invention. In some embodiments, a multi sprag arm variable anti-rotation friction element 430 may supply rotational resistance to a pushing shaft (for example see pushing shaft 422 FIG. 4B). The anti-rotational friction may facilitate relative rotation and/or telescoping of pushing shaft 422 with respect to a driver (for example driver 420). For example pushing shaft 422 may be threaded and driver 420 may include a threaded element, for example a threaded shaft and/or a nut.

Figure 4A:
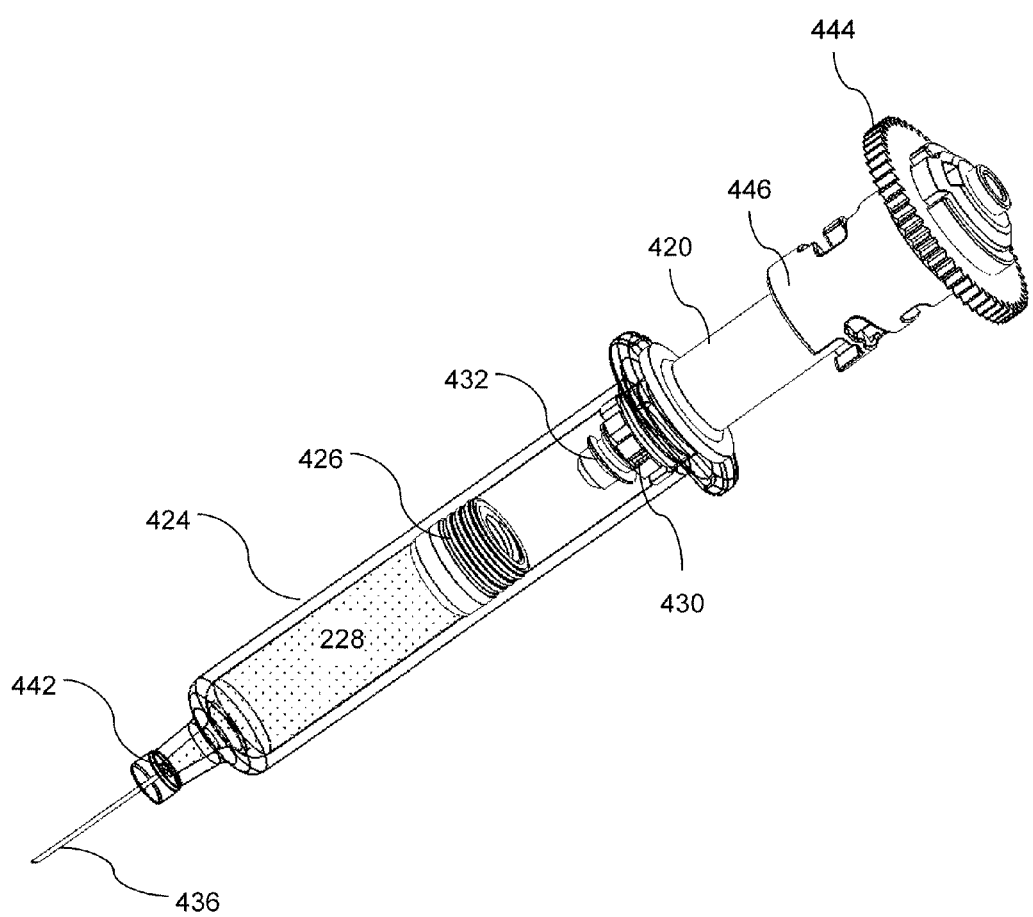
FIGS. 4A-4F are drawings of a plunger driving assembly and drug reservoir with a threaded plunger interface in accordance with embodiments of the current invention.

FIG. 4A illustrates a plunger driving assembly initially inserted into a proximal opening of a drug reservoir 424 in accordance with an embodiment of the current invention. In some embodiments, distal portion of the plunger driving assembly including for example a plunger interface 432 and/or variable resistance friction element 430 and/or a distal portion of pushing shaft 422. Optionally, when the plunger driving assembly is inserted, a plunger interface 432 remains distal to and/or disengaged from a plunger seal 426.

In some embodiments, a transmission gear 444, driver 420, a needle retraction lock 446 and a part of the proximal shaft 422 are located outside and/or proximal to reservoir 424. Optionally, the distal end of reservoir 424 includes a distal opening and a needle mount 442. The distal opening is optionally connected to a hypodermic needle 436. Optionally, the distal portion of reservoir 424 is filled with a drug 228. Plunger seal 426 separates and/or seals reservoir 424 between medicine 228 and a proximal portion and/or the proximal opening of the reservoir.

Figure 4B:
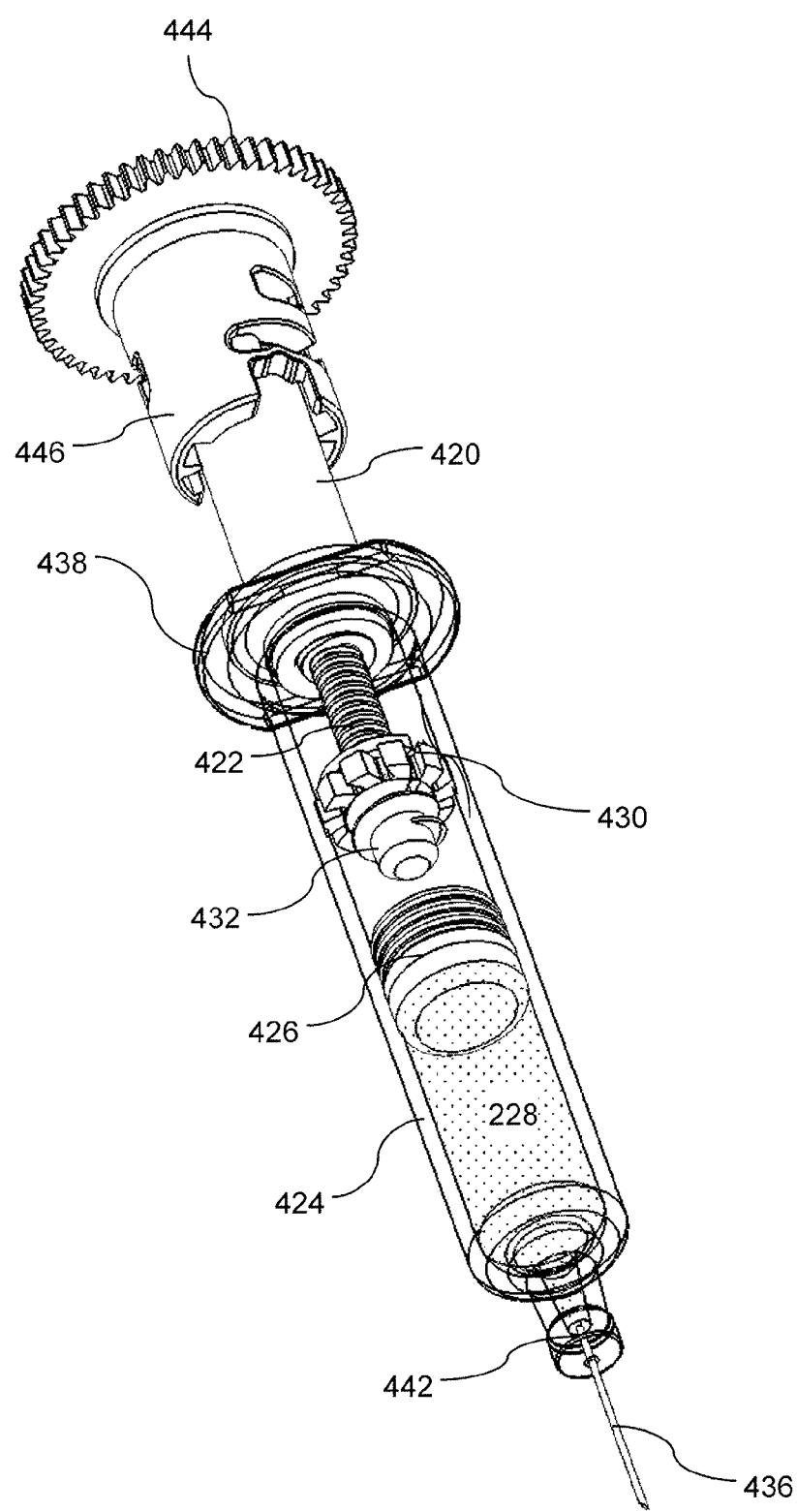

FIG. 4B illustrates a plunger driving assembly with the telescoping assembly beginning to open, advancing plunger interface 432 towards plunger seal 426 in accordance with an embodiment of the current invention. In some embodiments, after insertion, the telescoping assembly may be extended to advance interface 432 toward plunger seal 426 and/or to engage interface 432 to plunger seal 426.

In some embodiments, interface 432 is advanced by rotating transmission 444 and/or retraction lock 446 and/or driver 420 with respect to reservoir 424. Driver 420 is optionally threadably engaged to pushing shaft 422. In some embodiments, friction between friction element 430 and the inner walls of reservoir 424 inhibits rotation of pushing shaft 422 such that rotating driver 420 results in relative rotation between driver 420 and pushing shaft 422. Relative rotation of driver 420 and pushing shaft 422 optionally advances pushing shaft 422 and/or interface 432 towards plunger seal 426.

In some embodiments, interface 432 advances until it contacts plunger seal 426. When interface 432 contacts plunger seal 426, interface 432 may become linearly linked to plunger seal 426 (for example in that further linear advancement of interface 432 advances plunger seal 426)

and rotationally independent of plunger seal 426 (in that rotation of interface 432 does not rotate plunger seal 426). In some embodiments, distal advancement optionally stops due to the normal force between interface 432 and plunger seal 426 and/or friction force between plunger seal 426 and the walls of reservoir 424 and/or the normal forces between drug 228 and plunger seal 426. Optionally, rotation of driver 420 while interface 432 does not advance overcomes friction between friction element 430 and the walls of reservoir 424 and/or causes rotation of interface 432. For example, rotation of interface 432 may screw it into plunger seal 426.

In some embodiments, when interface 432 is fully screwed into plunger seal 426, interface 432 becomes rotationally linked to plunger seal 426 (for example in that further rotation of interface 432 rotates plunger seal 426). In some embodiments, rotation of interface 432 optionally stops due to the combined frictional resistance to rotation of interface 432 and plunger seal 426 with respect to the walls of reservoir 424. Optionally, rotation of driver 420 while interface 432 does not rotate overcomes resistance to axial motion and/or plunger seal 426 begins to move axially and/or discharges the drug from the distal opening of the reservoir (for example through needle 436). In some embodiments, reservoir 424 may include a flange 438. For example, flange 438 may extend out from a rear portion of reservoir 424.

Figure 4C:
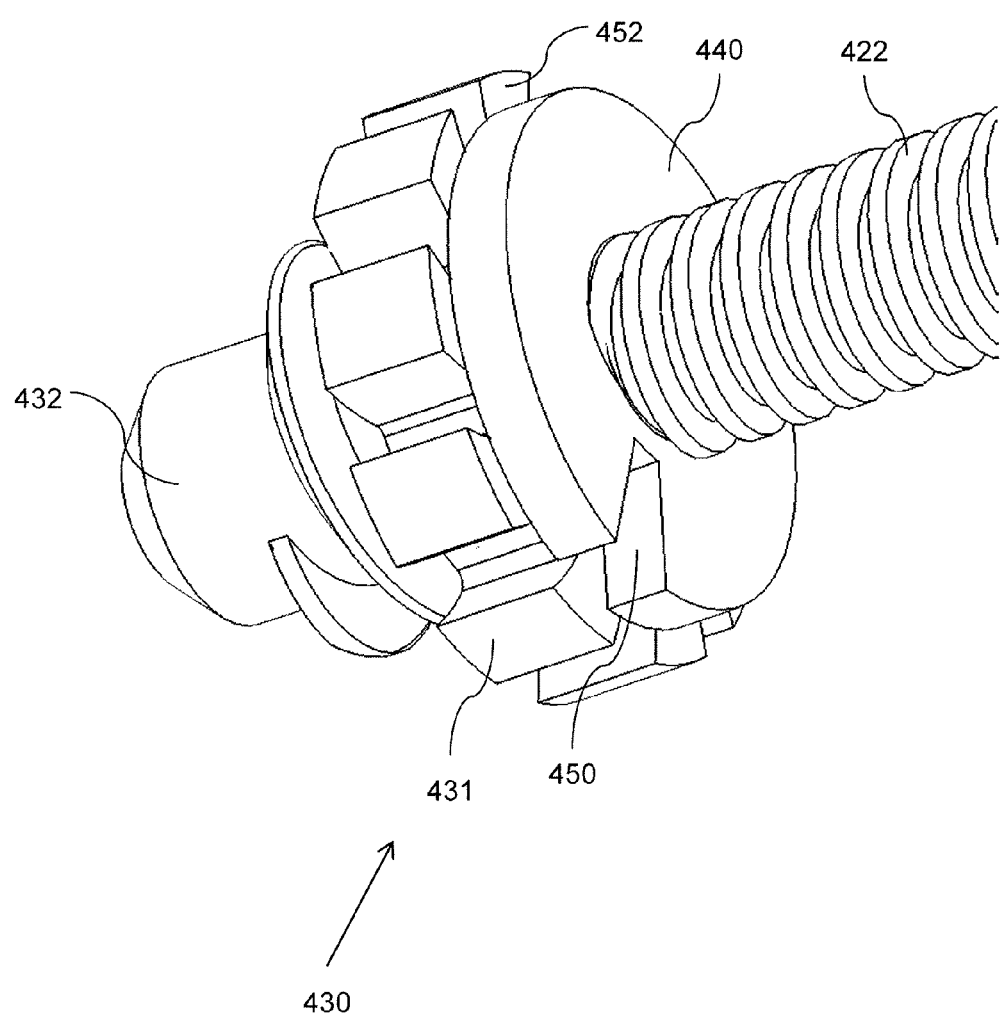

FIG. 4C is a close up perspective view of a distal end of a pushing shaft including a plunger interface 432 and a friction element 430 in accordance with an embodiment of the current invention. In some embodiments, an anti-rotation assembly may include a vent 450. For example, vent 450 may allow air to escape the zone between plunger seal 426 and interface 432 for example as interface 432 approaches plunger seal 426.

In some embodiments, a stabilizing base 440 may limit proximal movement of friction element 430 and/or determine the axial relationship of interface 432 and/or shaft 422 to friction element 430 and/or direct bowing and/or buckling of a radial element 452. For example, base 440 prevents radial elements 452 from buckling proximally and/or disengaging from the walls of reservoir 424. Optionally, there is a friction surface 431 on an external end of at least on radial element 452. For example, friction surface 431 may be held in contact with an interior wall of the reservoir.

Figure 4D:
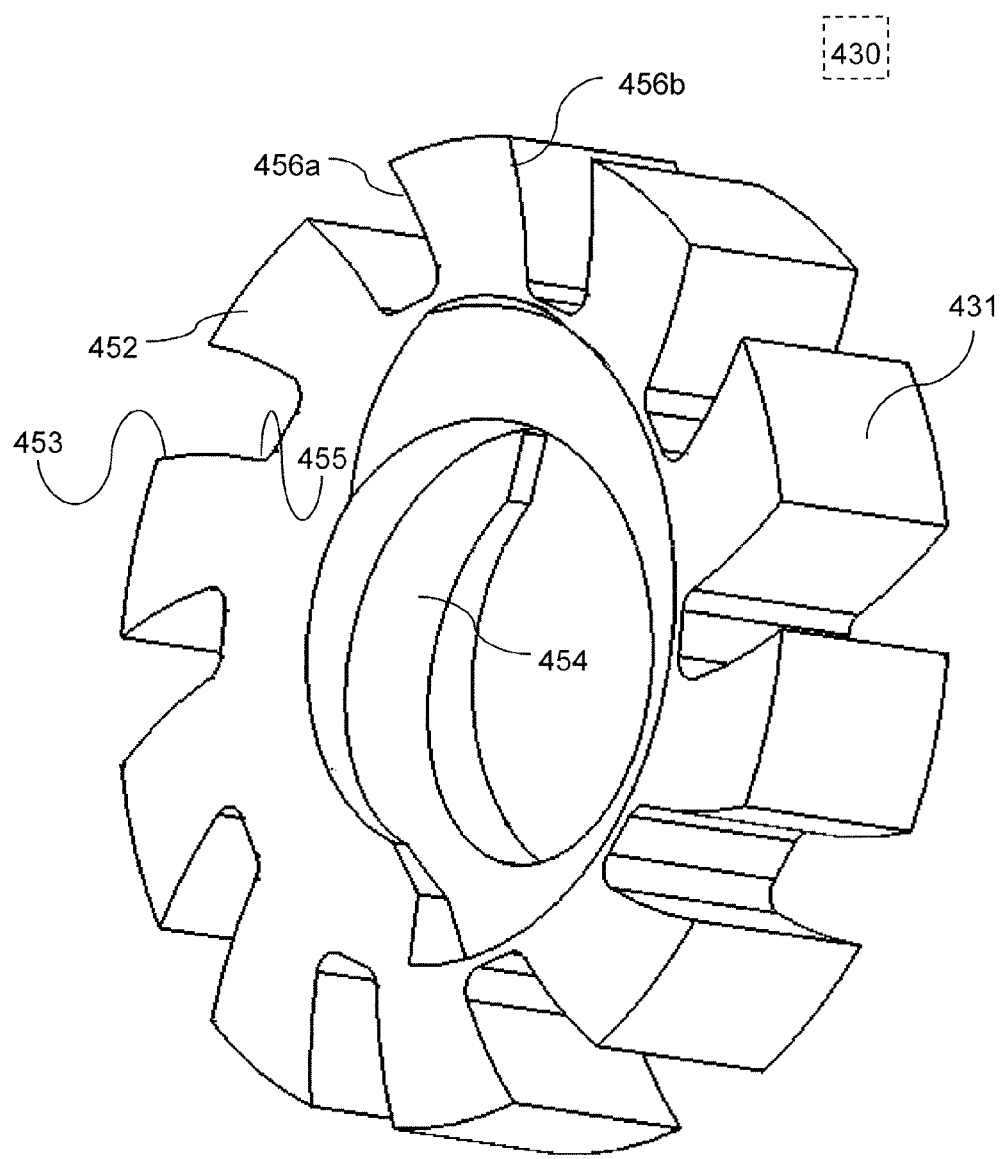

FIG. 4D is a close up perspective view of a friction element 430 in accordance with an embodiment of the current invention. For example, element 430 is optionally a flexible disk shaped element with independent flexible radial elements 452, for example sprags. Optionally, each sprag includes a friction surface 431 for contacting the walls of reservoir 424. For example, each sprag is tilted off the radial direction towards the direction of inhibited movement. Optionally, friction surface 431 is on the outer end of the each radial element 452. For example, the outer end of each radial element 452 spread as it radiates outward and/or the outer end (head 453) of each sprag may be wider than its central end (stem 455).

In some embodiments, radial elements 452 are angled against an inhibited direction of rotation. For example, the inhibited direction of rotation may be the direction of rotation of driver 420 for extension of the telescoping assembly. Optionally, when driver 420 is rotating in a direction to expand the telescoping assembly (and/or advance pushing shaft 422) and frictional element 430 begins to rotate in the direction of rotation of driver 420, sprag type radial elements 452 get wedged against the walls of reservoir 424. Optionally, when driver 420 is rotating in a direction to expand the telescoping assembly (and/or advance pushing shaft 422) and frictional element 430 begins to rotate in the direction of rotation of driver 420 friction is increase between frictional element and reservoir 424 inhibiting the rotation of shaft 422 and/or facilitating relative rotation between driver 420 and shaft 422 and/or facilitating advancement of shaft 422. In some embodiments, a sprag 452 may be anisotropic. For example, the angle of attack of a leading edge 456a may be steeper than the angle of attack of a trailing edge 456b. For example, the mean angle of attack of sprag 452 may range between 80 and 90 degrees while the mean difference between the leading 456a and trailing 456b edges may range between 1 and 9 degrees. For example, the mean angle of attack of a sprag may range between 60 and 80 degrees while the mean difference between the leading and trailing edges may range between 1 and 40 degrees. For example, the mean angle of attack of a sprag may range between 20 and 60 degrees while the mean difference between the leading and trailing edges may range between 1 and 70 degrees.

In some embodiments, friction element 430 may be made of rubber, elastomer and/or silicone for example of hardness shore 00 scale approximately 50. For example, the hardness may range between shore 00 scale 10 to 30 and/or 40 to 60 and/or 60 to 100 and/or shore A scale 60 to 100. Optionally, the unstressed diameter of friction element 430 is slightly larger than the inner diameter of reservoir 424. For example, the unstressed outer diameter of element 430 may be approximately 9.1 mm while the inner diameter of reservoir 424 may be approximately 8.65 mm. Optionally, the inner diameter of a reservoir may range between 1 to 4 mm and/or between 4 to 7 mm and/or between 7 to 10 mm and/or between 10 to 15 mm and/or between 15 to 30 mm. Optionally, the outer diameter of a friction element may range between 100% to 103% and/or 103% to 107% and/or 107% to 120% and/or 120% to 150% the internal diameter of the reservoir. In some embodiments, friction element 430 may have a closed diameter at the base (stem 455) of sprags 452 of approximately 6.3 mm and/or the length of sprags 452 (in the radial direction) may be approximately 1.4 mm. For example, the thickness (along the length of reservoir 424) of element 430 and/or sprags 452 may be 2 mm and/or radial length of the head of sprags 452 may be approximately 1.65 mm and/or the surface 431 area of each sprag 452 in contact with the inner wall of reservoir 452 may be approximately 2+1.65=3.3 mm². In some embodiments, the length of a sprag element may range for example between 1 and 10% the diameter of the reservoir and/or between 10 to 20% the diameter of the reservoir and/or between 20 to 40% the diameter of the reservoir and/or between 40 to 70% the diameter of the reservoir and/or between 70 to 100% the diameter of the reservoir. In some embodiments, the width of a friction element may range for example between 1 to 5% and/or between 5 to 15% and/or between 15 to 25% and/or between 25 to 50% and/or between 50 to 75% and/or between 75 to 150% and/or between 150 to 600% the diameter of the friction element.

In some embodiments, friction element 430 may include a mount for connection to pushing shaft 422 and/or to interface 432. For example, shaft mount 454 of friction element 430 includes an internally threaded aperture that threadably mates to an external threads 462 of plunger interface 432 (see for example FIG. 4E).

Figure 4E:
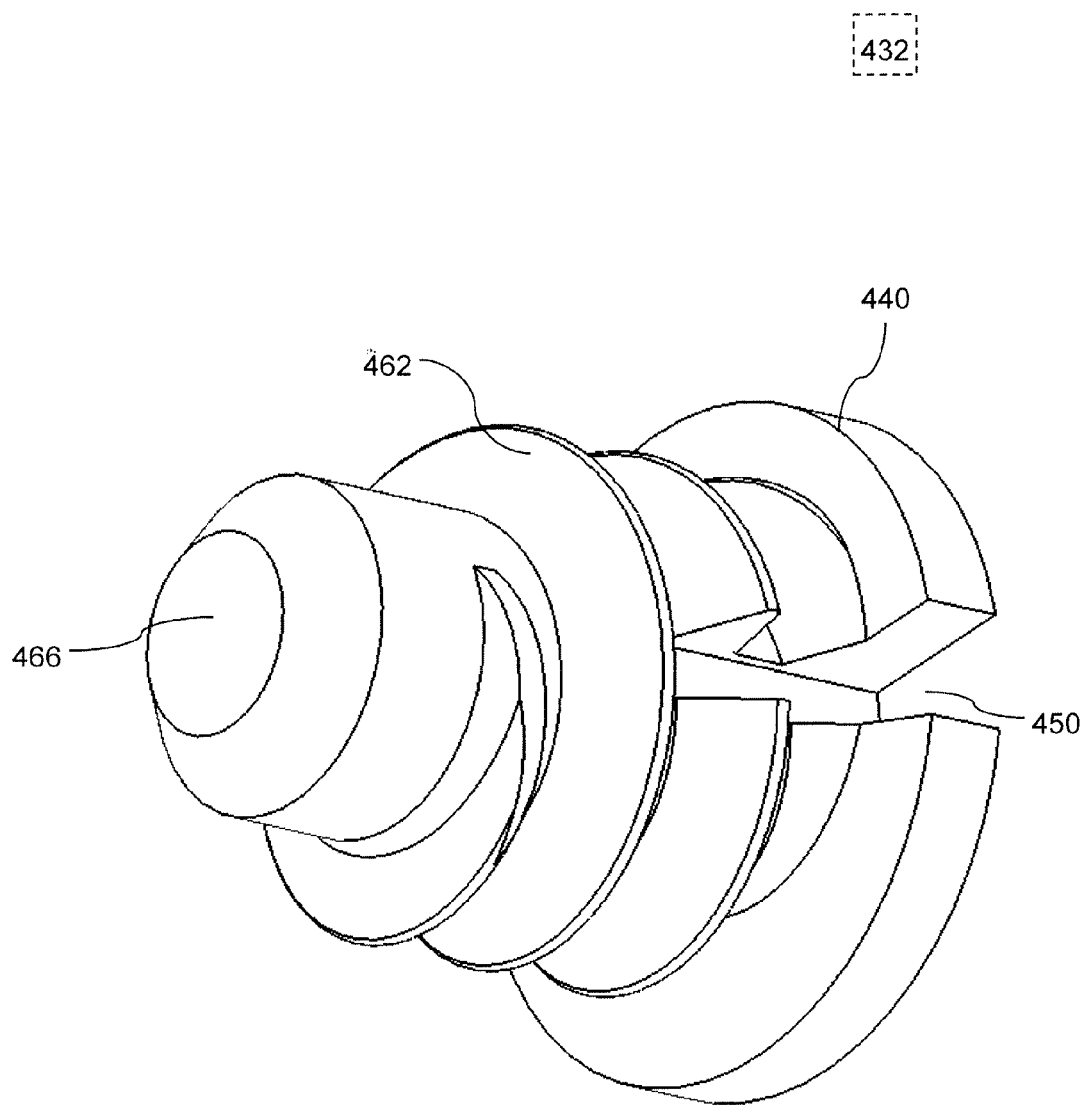

FIG. 4E is a close up perspective view of plunger interface 432 in accordance with an embodiment of the current invention. For example, interface 432 is optionally a hard element (for example made of molded plastic) with a tapered screw thread 462 for attaching to plunger seal 426 and/or friction element 430. Optionally, interface 432 includes a tapered distal face 466 and/or a proximal base 440 and/or a vent 450. Optionally vent 450 includes a slit in base 440. Optionally, slit 450 is positioned to align with a space between radial elements 452. Alternatively or additionally, a friction element may include a vent. For example, when the friction element is mounted on interface 432, the vent of the friction element may be aligned with vent 450.

In some embodiments, friction element 430 may include a mount for connection to pushing shaft 422 and/or to interface 432. For example, shaft mount 454 of friction element 430 includes an internally threaded aperture that threadably mates to an external threads 462 of plunger interface 432 (see for example FIG. 4E).

Figure 4F:
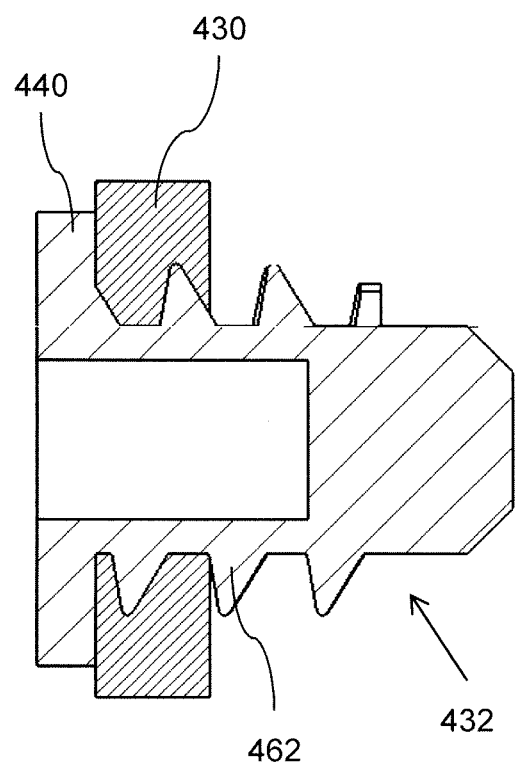

FIG. 4F is a cross sectional view of friction element 430 mounted on an adapter 432 in accordance with an embodiment of the present invention. For example, screw threads 462 are smaller at the insertion point (the distal end) and grow as one moves proximally. The rear (proximal) face of the teeth is optionally at a sharper angle (for example between 70 to 95 degrees from the axis of adaptor 432) than the front (distal) face of the teeth (which range for example at an angle between 115 to 145 degrees from the axis of adaptor 432).

Linear Motion Sensitive Sprags

Figure 5:
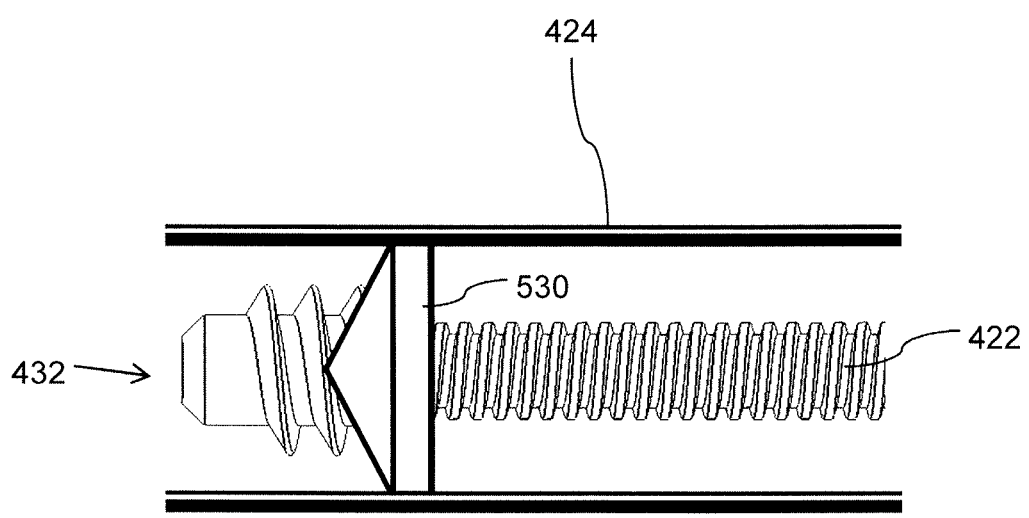
FIG. 5 is a perspective driving of a plunger pushing rod and friction element for facilitating forward linear motion in accordance with embodiments of the current invention.

FIG. 5 is a perspective drawing of a plunger pushing rod and friction element for facilitating forward linear motion in accordance with embodiments of the current invention. Optionally, friction element 530 is angled backwards (for example proximally). For example, advancement of shaft 422 the angle of attack of element 530 would be greater than 90 degrees. Optionally, advancement of shaft would reduce the normal force and/or the friction between friction element 530 and the wall a reservoir 424. Optionally, when shaft 422 is rotating but not advancing, the friction between element 530 and reservoir 424 is high, inhibiting rotation. Optionally, as shaft 422 advances in reservoir 424, the shape of element 530 causes a reduction in friction facilitating the advancement.

Friction Disk with Anti-Rotation Beam

Figure 6A:
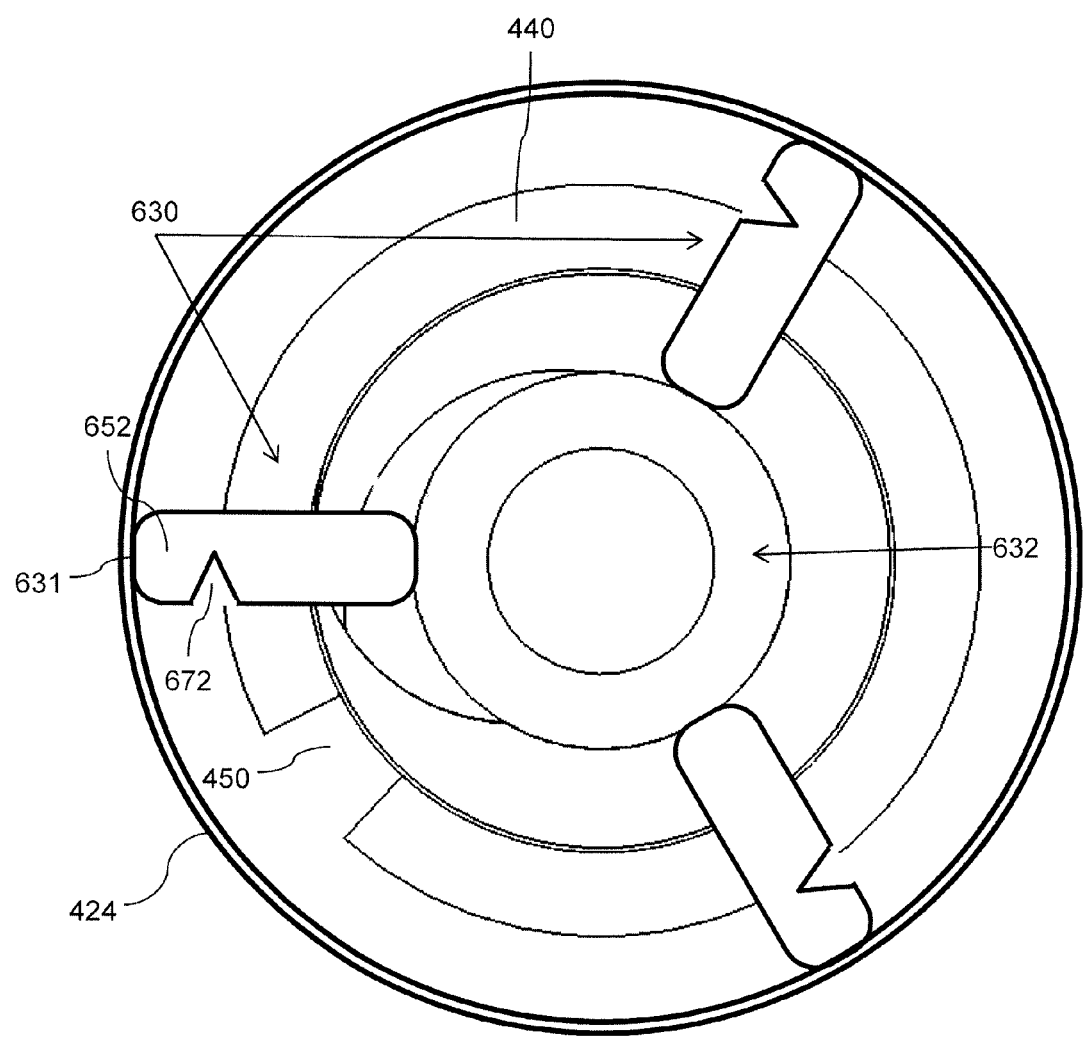
FIGS. 6A-6B are cross sectional views of a plunger pushing rod including flexible beam anisotropic friction elements in accordance with embodiments of the current invention.

FIG. 6A is cross sectional view of a plunger pushing rod including flexible beam anisotropic friction elements in accordance with embodiments of the current invention. In some embodiments, a friction element 630 may include an anisotropic bending beam 652. For example, when beam 652 is bent in an inhibited direction it may not bend away and/or it may get wedged between a plunger interface 632 and the walls of reservoir 424. For example, when beam 652 is bent in a non-inhibited direction, beam 652 may bend out of the way and/or reduce friction. In FIG. 6A elements 652 are illustrated in a relatively unstressed state.

In some embodiments, a beam may have anisotropic compressibility and/or extensibility. For example, beam 652 has a cut out section 672. The side of the beam with the cut out extends and/or compresses more easily than the opposite side.

Figure 6B:
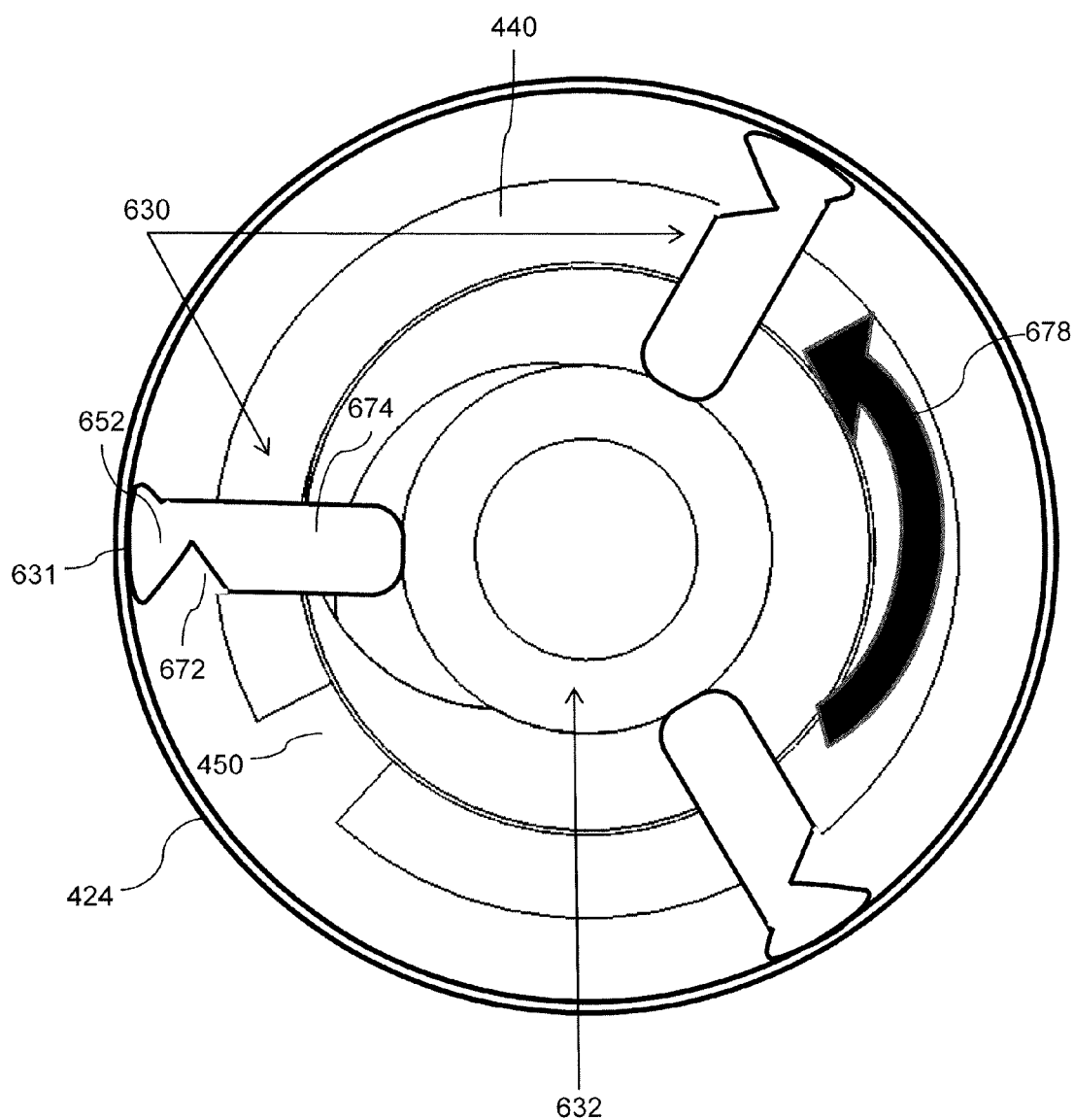

FIG. 6B illustrates element 652 in a stressed state due to rotation of interface 632 in an inhibited direction 678 in accordance with an embodiment of the present invention. Optionally, when element 652 is stressed, cut out section 672 may tend to expand and/or contract while uncut side of the beam may tend to buckle and/or bend. Optionally, stress due to rotation in the inhibited direction 678 causes cut out section 672 to open wedging surface 631 against reservoir 424 increasing a normal force and/or a friction between surface 631 and reservoir 424.

Pressure Sensitive Friction Element

Figure 7A:
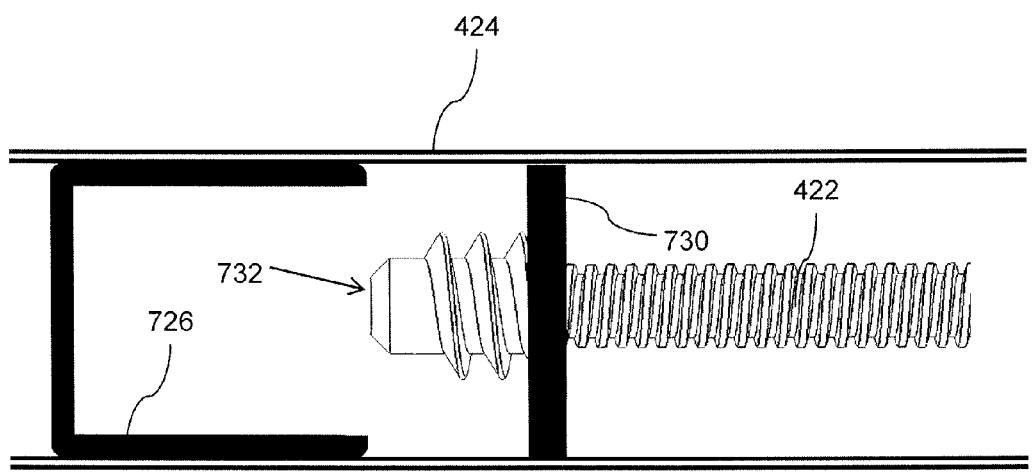
FIGS. 7A-7B are side views of a plunger pushing assembly with reduced friction when engaged to a plunger in accordance with embodiments of the current invention.
Figure 7B:
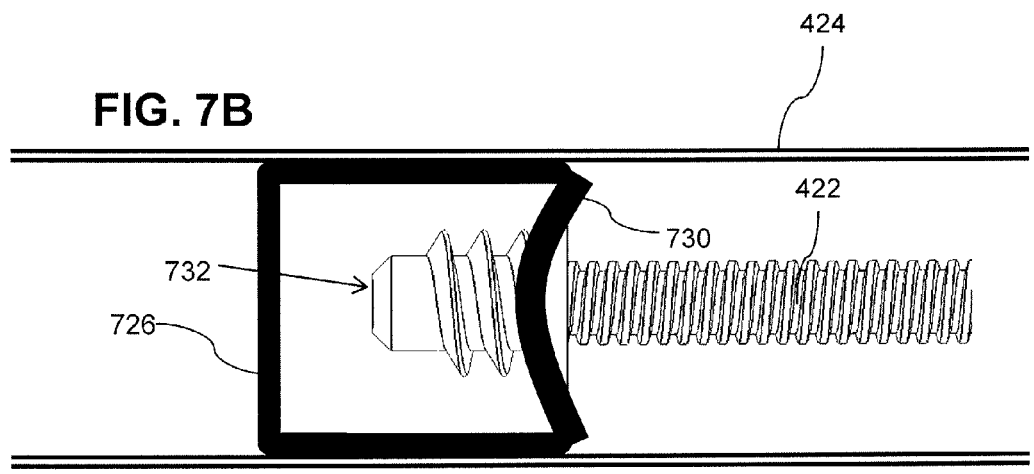

FIGS. 7A-7B are side views of a plunger pushing assembly with reduced friction when engaged to a plunger in accordance with embodiments of the current invention. For example, a friction element 730 may be sized to contact a wall of a drug reservoir and/or produce friction with the wall inhibiting rotation of a plunger pushing shaft 422 and/or a plunger interface 732. Optionally, when interface 732 engages a plunger 726, friction between element 730 and the reservoir may be reduced and/or the resistance to advancement of the plunger may be reduced.

FIG. 7A illustrates plunger interface 732 and friction element 730 while disengaged from a plunger in accordance with an embodiment of the current invention. In some embodiments, shaft 422 may be advanced through reservoir 424 by rotation of a driver relative to shaft 422. As interface 732 approaches plunger 726, friction element contacts the interior walls of reservoir 424 and/or inhibits rotation of shaft 422 and/or facilitates the relative rotation of the driver with respect to shaft 422.

FIG. 7B illustrates plunger interface 732 and friction element 730 while engaged to a plunger in accordance with an embodiment of the current invention. In some embodiments, when interface 732 engages plunger 726, an element (for example the hard side walls of the plunger and or a bowl shaped and/or annular projection) deform friction element 730. Deformation of friction element 730 optionally reduces and/or eliminates contact between friction element and reservoir 424. For example, deformation of friction element 730 may reduce and/or substantially nullify friction between element 730 and reservoir 424. Optionally, when plunger interface 732 is engaged with plunger 726, friction between plunger 726 and reservoir 424 may inhibit rotation of shaft 422 and/or facilitate advance of shaft 422 and/or plunger 726. In some embodiments, reduction of the friction between element 730 and reservoir 424 may reduce the load on a plunger pushing assembly. For example, interface 732 may be engaged to plunger 726 while a device is discharging a drug. Reduction of friction between element 732 and reservoir 424 optionally reduces the load on the plunger pushing system while discharging the drug.

In some embodiments, advancement of the plunger pushing assembly may proceed through a few friction stages and/or configurations. For example, while interface 732 is distanced proximally from plunger 726, the resistance to rotation caused friction between element 730 and reservoir 424 may be enough to prevent rotation of shaft 422. With shaft 422 rotationally immobile, rotation of a driver may produce relative rotation between the driver and shaft 422 and/or advancement of shaft 422.

In some embodiments, shaft 422 advances until interface 732 contacts the proximal side of plunger 726. Once interface 732 contacts the proximal side of plunger 726 rotation of the driver and resistance to rotation by friction element 730 may be enough to overcome resistance to advance of plunger 726. Subsequently, interface 732 is driven forward, driving forward plunger 726 and discharging the medicine. Alternatively or additionally, when interface 732 contacts the proximal side of plunger 726, resistance to advance of plunger 726 may be enough to stop advance of shaft 422. While resistance of plunger 726 prevents advance of interface 732, torque optionally overcomes rotation resistance of element 730. For example, overcoming rotational resistance may cause interface 732 to rotate and/or be screwed into the proximal end of plunger 726 and/or engage plunger 726.

In some embodiments, once interface 732 is engagement of interface 732 to plunger 726 may prevent rotation of interface 732 with respect to plunger 726. Friction between plunger 726 and reservoir 424 may prevent further rotation of shaft 422, facilitating relative rotation of shaft 422. Prevent rotation of interface 732 optionally facilitates rotation a driver in relation to shaft 422 optionally facilitating further advance of plunger seal 426.

Plunger Interface

Figure 8:
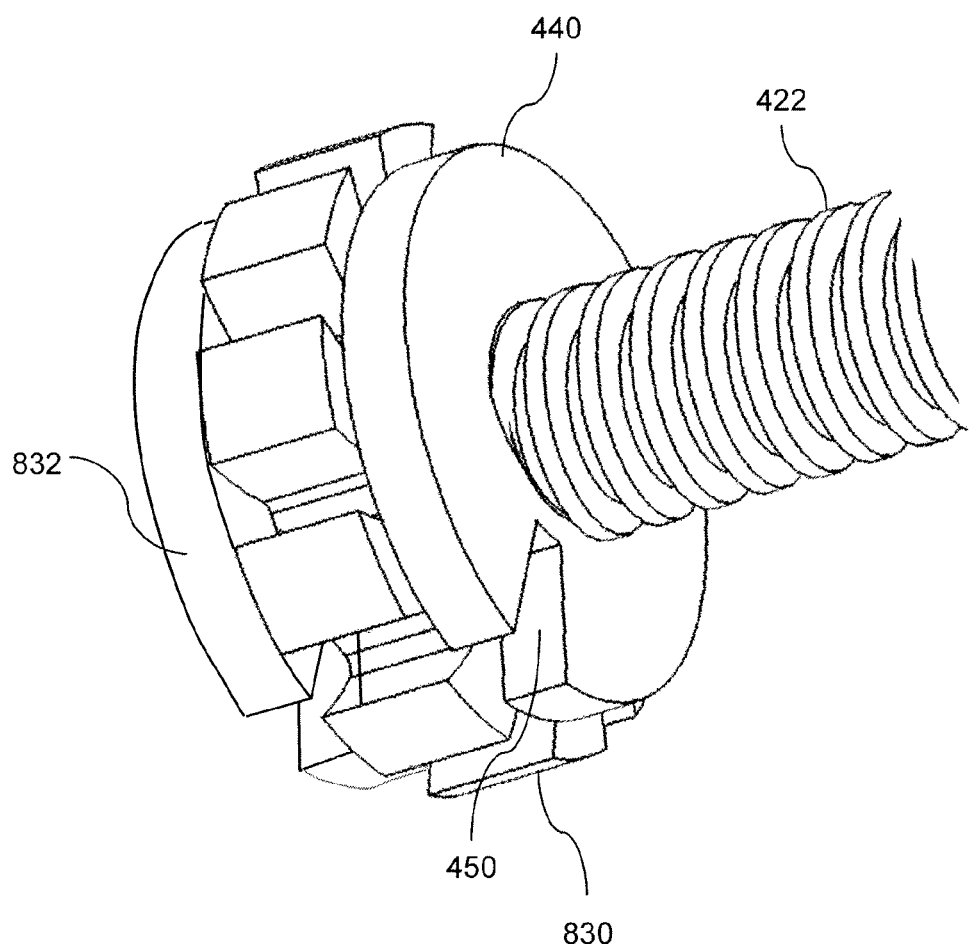
FIG. 8 is a perspective view of a plunger pushing rod including a sprag friction elements and a ram plunger interface in accordance with embodiments of the current invention.

FIG. 8 is a perspective view of a plunger pushing rod including a sprag friction elements and a ram plunger interface in accordance with embodiments of the current invention. In some embodiments, a plunger interface will transfer linear forces between a plunger and a pushing shaft 422. Optionally, the interface will transfer limited or negligible rotational torque between the plunger and the pushing rod. For example, a ram 832 may push a plunger along an axis of a drug reservoir (for example distally). Ram 832 may transfer little or no torque around the axis. For example, embodiments, ram 832 may not be rotationally fixed to shaft 422 and/or to the plunger. Torque is optionally transferred between shaft 422 and the plunger by friction. Alternatively or additionally, there may be a rotating element (for example a pivot and/or an axel) between shaft 422 and ram 832 limiting transfer of torque. Optionally, rotational resistance of friction element 830 will be high enough to prevent a driver from rotating shaft 422 under the dual load of linear resistance of friction element 830 and the plunger (resistance to linear movement of the plunger may include for example friction between the plunger and the reservoir and/or resistance to discharge of the drug).

Friction Disk with Anti-Rotation Sprag Ribs

Figure 9:
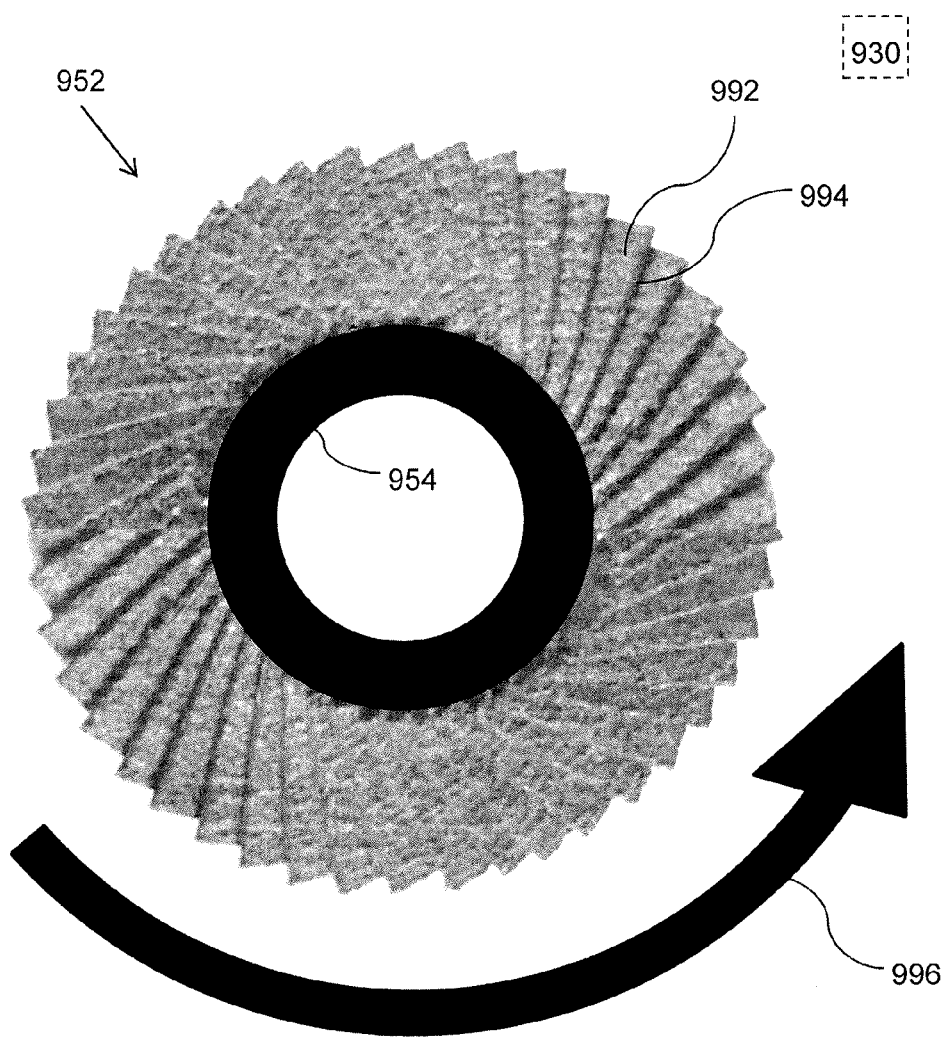
FIG. 9 is a perspective view of a plunger pushing rod including virtual sprag friction elements in accordance with embodiments of the current invention.

FIG. 9 is a perspective view of a friction element 930 including virtual sprag friction elements in accordance with embodiments of the current invention. In some embodiments, a radial element 952 may be constructed of angled layers of connected sheets 992. Sheets 992 are optionally angled toward the inhibited direction 996 of rotation. When the periphery of element 930 are in frictional contact with an immobile reservoir wall, rotation of element 930 in the inhibited direction 996 optionally spreads sheets 992 and/or increase a surface area of friction. Alternatively or additionally, rotation in the inhibited direction 996 pushes against joints 994 which are virtual sprag elements that are optionally stiffer than the sheets, for example increasing a normal force between friction element 930 and a wall of a reservoir. Alternatively or additionally, virtual sprag elements may include a thickened rib angled against the inhibited direction and/or a rib of a stiffer material than the rest of the disk angled against the direction of inhibited movement. Optionally, friction element 930 optionally includes a shaft mount 954.

Friction Element with Rollers

Figure 10A:
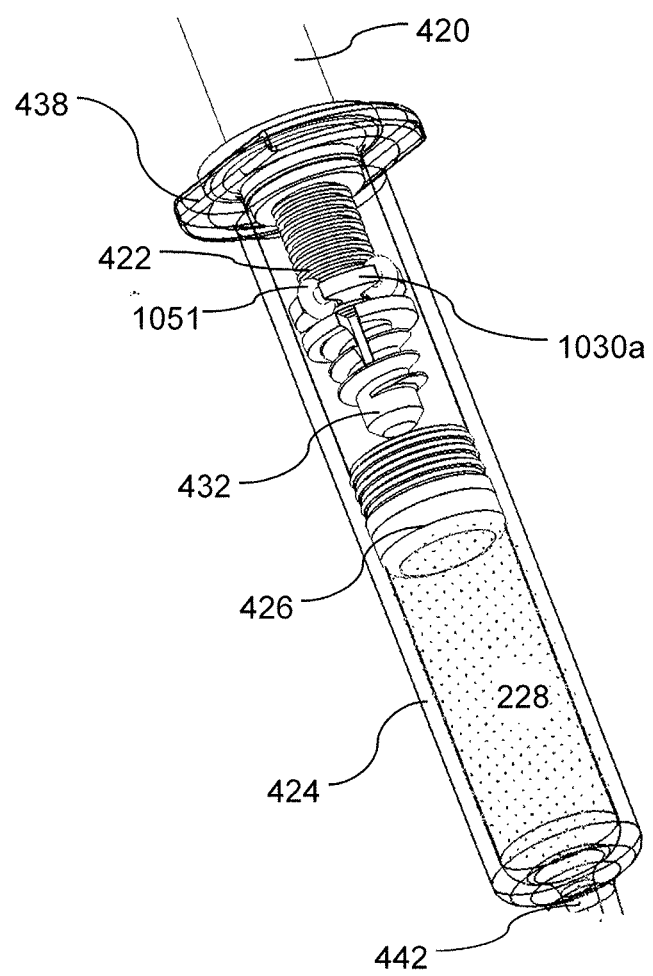
FIG. 10A is a perspective view of a cartridge including a wheeled friction element in accordance with an embodiment of the current invention.

FIG. 10A is a perspective view of a friction element 1030a including rolling element 1051 in accordance with embodiments of the current invention. For motion in the preferred direction, rolling element 1051 may roll, allowing motion with minimal friction whereas for motion in the non-preferred direction. For example, friction element 1030a may move axially inside reservoir 424 with a friction force of a hundredth or less than the force necessary to rotate element 1030a around the axis of reservoir 424. For example, a rolling element may be round and/or spherical and/or cylindrical and/or tapered. A rolling element may include a wheel and/or an axel and/or a bearing and/or a race and/or a cage.

Figure 10B:
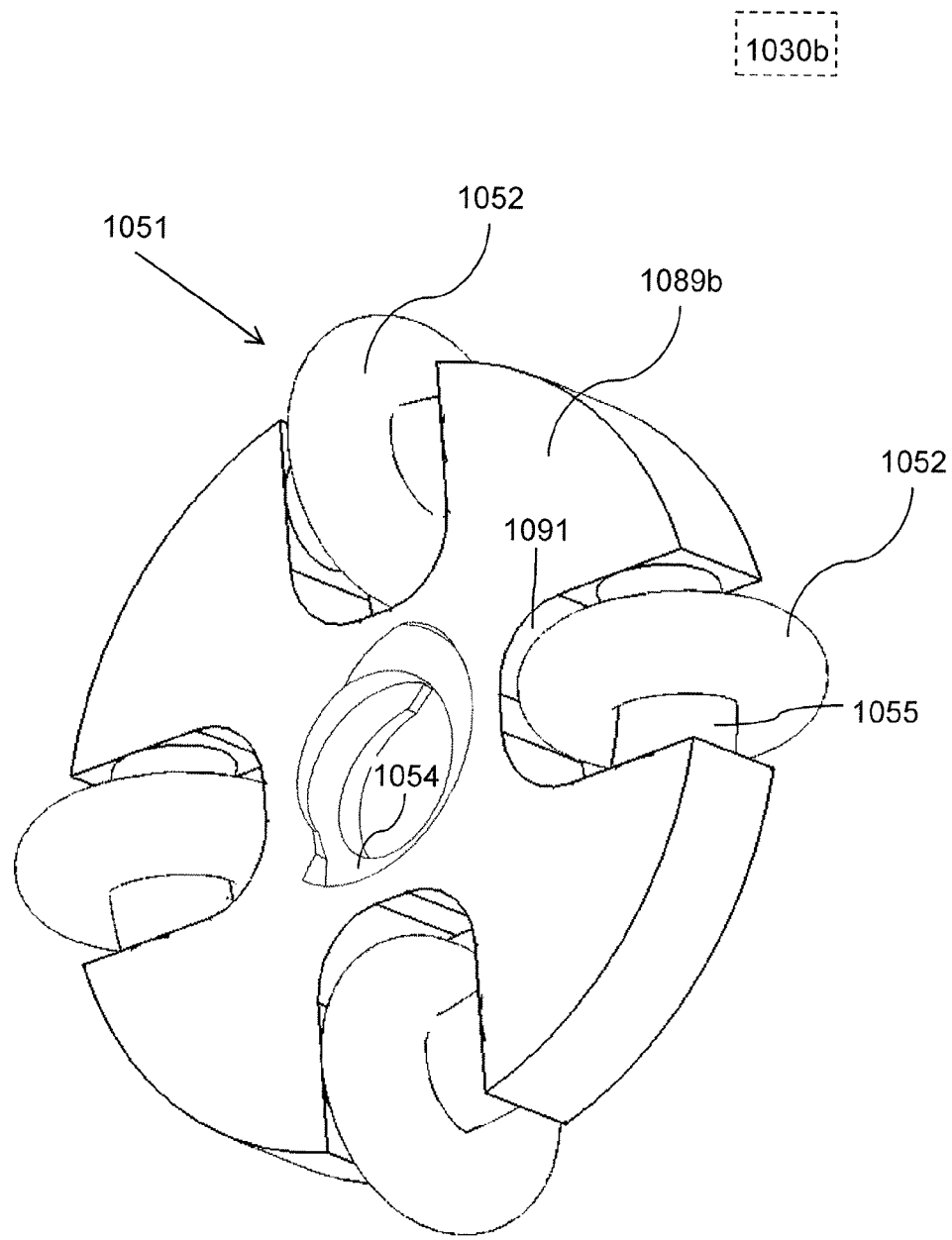
FIG. 10B is a perspective view of a wheeled friction element with a shaft mount in accordance with an embodiment of the current invention.

In some embodiments, for example as illustrated in FIG. 10B, rolling element 1051 may include a wheel 1052. For example, during movement in a preferred direction, for example as element 1030b moves linearly along the axis of reservoir 424, wheel 1052 may rotate around an axel 1055. Optionally, a rolling element may be inside an indentation and/or a ball cage 1091. For example, cage 1091 optionally includes an indentation in a connecting element 1089b. For example, connecting element 1089b may include a disk and/or cylindrical connector between a drive screw and/or a plunger adapter. Alternatively or additionally, friction element may be built into a driving element and/or a plunger adapter. For example, a wheel and/or an axel and/or a race and/or a cage may be built into the plunger adapter and/or the drive element.

Figure 10C:
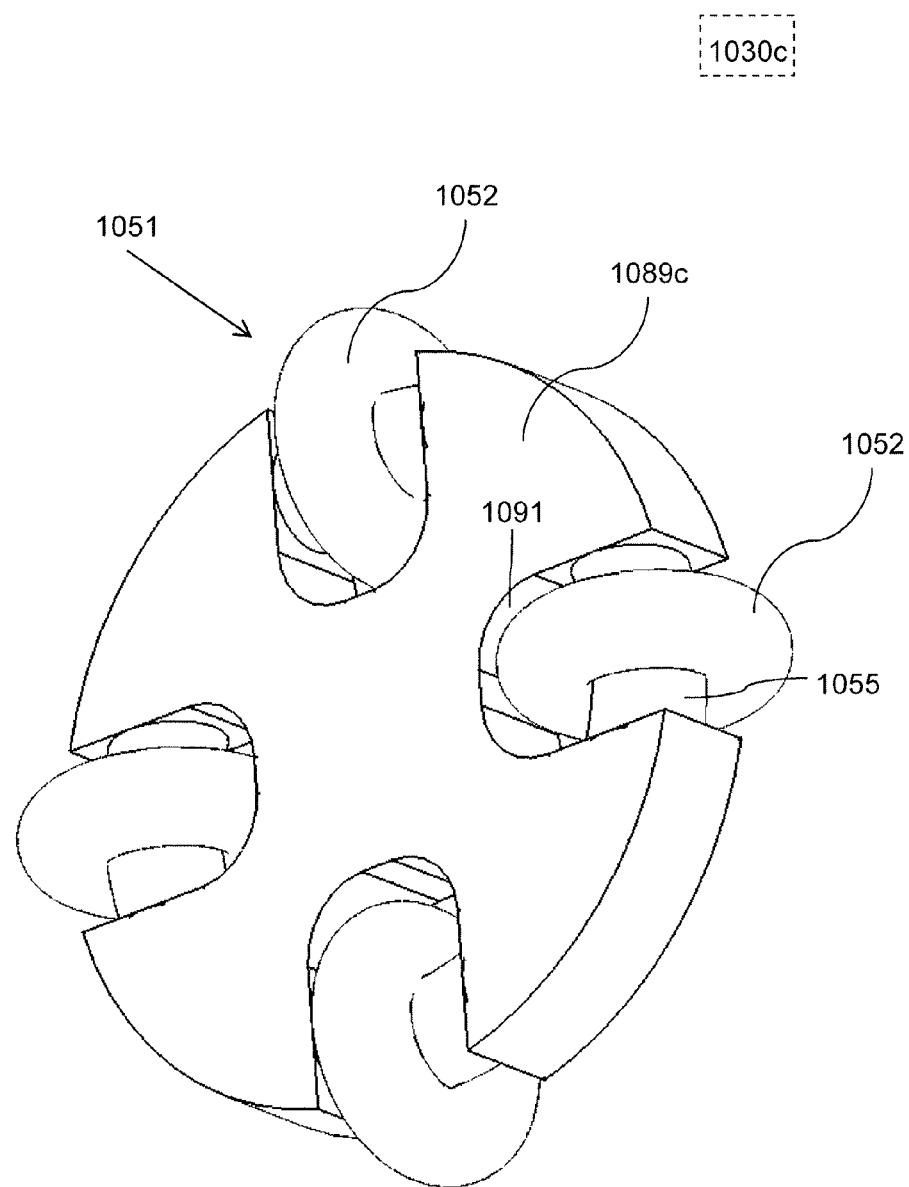
FIG. 10C is a perspective view of a wheeled friction element without a shaft mount in accordance with an embodiment of the current invention.

Some embodiments of an anti-rotational element 1030b, a connecting element 1089b may include a shaft mount 1054, for example as illustrated in FIG. 10B. Additionally or alternatively, in some embodiments of an anti-friction element 1030c, a connecting element 1089c may not have a shaft mount, for example as illustrated in FIG. 10C. For example, connecting element fit between a driving shaft and/or a plunger.

Friction Element Preventing Rotation of Reservoir

Figure 11:
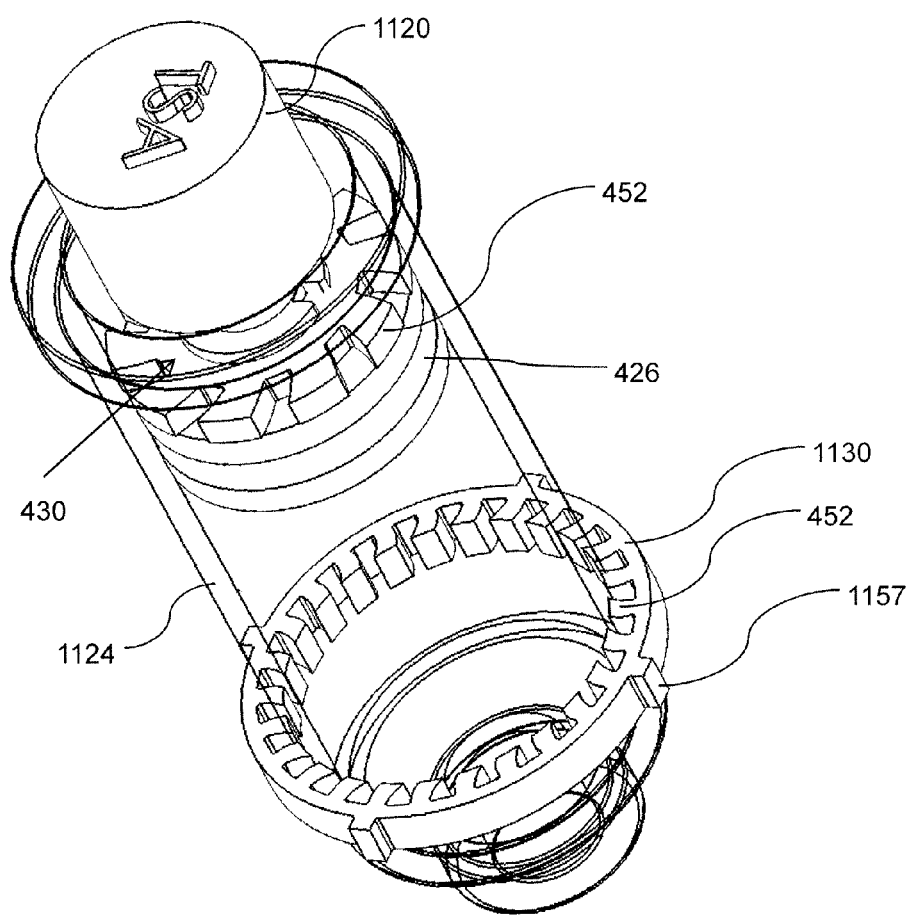
FIG. 11 is a perspective view of a cartridge held by an external friction annular element in accordance with an embodiment of the current invention.

FIG. 11 is a perspective view illustration of a drug reservoir with an external anti-rotational friction element in accordance with an embodiment of the present invention. Optionally, an external friction element 1130 resists rotation of the reservoir with respect to a housing of a drug delivery device. For example, friction element 1130 has anisotropic friction with higher frictional resistance against movement in a non-preferred direction than in a preferred direction. For example, sprags 452 have enhanced friction to resist rotation of reservoir 1124 in a non-preferred direction. Optionally, reservoir can easily be slid longitudinally into element 1130, but once in place is difficult to move in a non-preferred direction (for example to rotate against sprags 452 and/or to remove reservoir 1124).

In some embodiments, element 1130 may have the form of a ring surrounding reservoir 1124. Optionally, sprags 452 radiate inward from the ring towards the outer wall of reservoir 1124.

In some embodiments, a system may include two directionally preferential friction elements. For example, friction element 430 may prevent rotation of a plunger driving shaft. For example, element 430 facilitates movement of a plunger driver by a shaft driver 1120. In some embodiments, sprags 452 of internal friction element 430 are oriented in the opposite direction from sprags 452 of external friction element 1130. For example, friction element 430 may prevent a plunger driver from rotating by applying a first torque in a first non-preferred direction (non-preferred with reference to inner element 430) to an inner wall of reservoir 1124. Optionally, element 1130 may prevent rotation of reservoir 1124 by providing an opposite torque to the outer wall of reservoir 1124. The second torque may inhibit rotation of reservoir 1124 in a second non-preferred direction. In some embodiments, the first and second non-preferred directions may be opposite in orientation.

In some embodiments, external friction element 1130 may include anchors 1157 to hold it in a drug delivery device. For example, anchors 1157 are protrusions molded into element 1130 that fit into indentations on the inner wall of a casing of a drug delivery device (for example casing 1259 as illustrated in FIG. 12B). Optionally, anchors 1157 inhibit movement of element 1130 with respect to the drug delivery device. Optionally, other means may be used to stabilize element 1130 with respect to a delivery device, for example glue and/or other sorts of anchors and/or fittings.

Figure 12A:
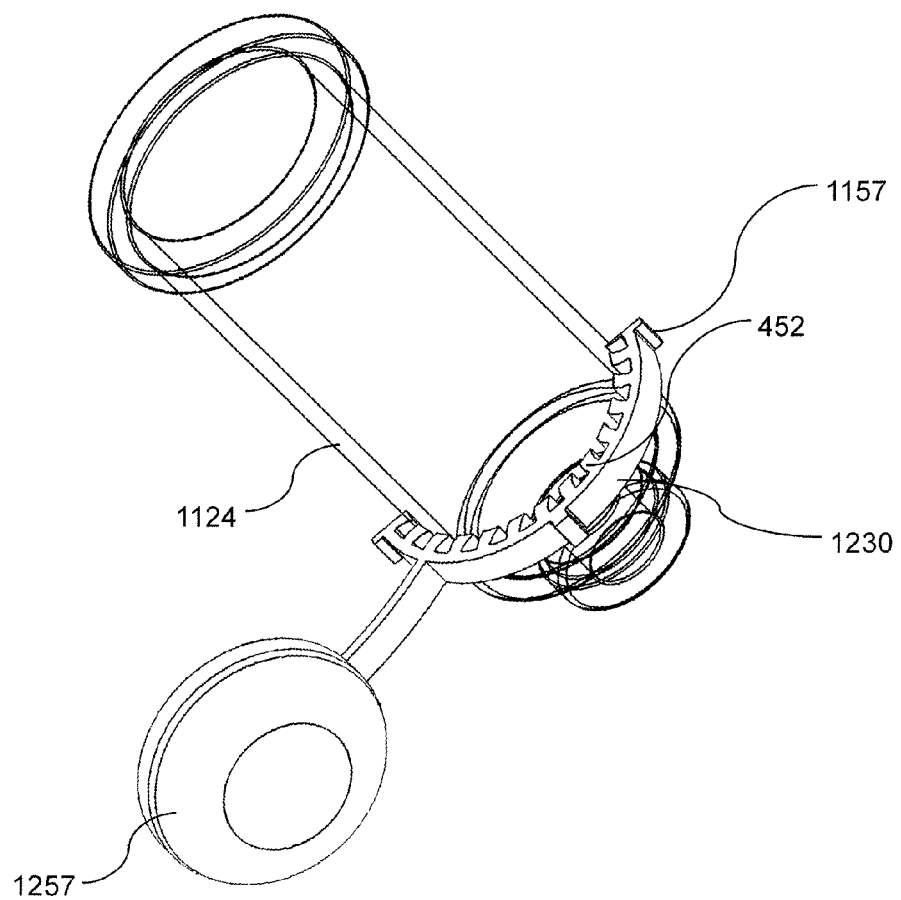
FIG. 12A is a perspective view of a cartridge including an external semi annular friction element in accordance with an embodiment of the current invention.
Figure 12B:
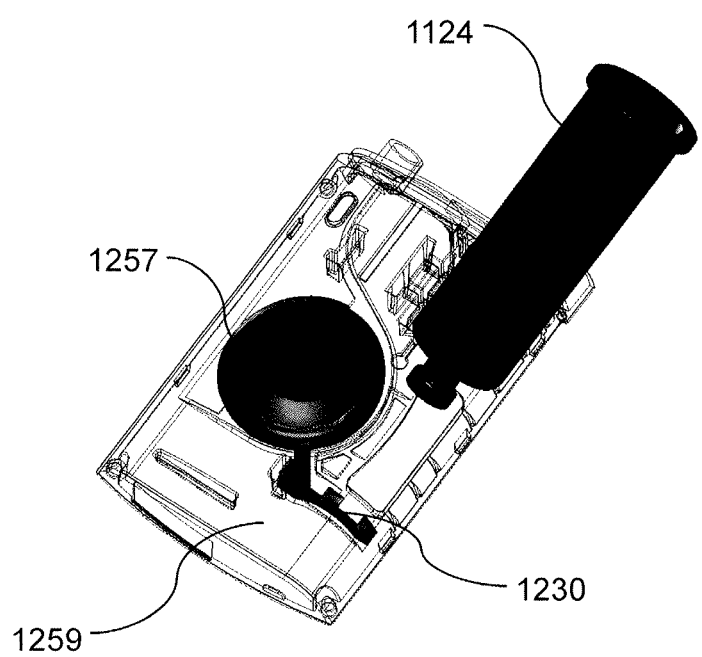
FIG. 12B is a perspective view of a cartridge including an external semi annular friction element installed into a drug delivery device in accordance with an embodiment of the current invention.

FIG. 12A is a perspective view illustration of a drug reservoir with an alternative external anti-rotational friction element 1230 in accordance with an embodiment of the present invention. Optionally, element 1230 only partially surrounds reservoir 1124. Element 1230 is optionally molded in one step with other elements of a drug delivery device. For example, element 1230 includes an elastomeric button cover 1257 for the delivery device.

FIG. 12B illustrates an internal view of friction element 1230 installed into a top half of a casing 1259 of a drug delivery device. Element 1230 optionally serves to inhibit rotation of reservoir 1124. Optionally, cover 1257 seals a hole in casing 1259 providing a water tight seal. The hole optionally provides access for a user to push an activation button of the device.

Optionally, an outer friction element may include various anisotropic friction elements as described herein above for example a sprag and/or an anisotropically bending beam and/or a clutch dog and/or a virtual element and/or an anisotropic friction surface. Friction to inhibit rotation of the reservoir may optionally be provided by multiple elements.

Exemplary Dimensions of a Drug Delivery Device

In some embodiments, the payload of a reservoir (for example a syringe) may include, for example between 0.5 and 2 ml and/or between 2 and 4 ml and/or between 4 and 5 ml of a drug and/or more. In some embodiments, the injector may discharge the entire payload as a single dose. A drug delivery device may include, for example, a pen injector, and/or an internally powered driver to drive the plunger and/or discharge the payload. For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or torque spring and/or a pressurized gas). For example, the driver may be designed to discharge the payload over a time period ranging between 20 and 120 seconds and/or between 120 and 600 seconds and/or longer. In some embodiments, discharge may be driven by a driver. An internally powered driver may be powered by various mechanisms including for example a motor (including for example a DC motor, an actuator, a brushless motor) and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the current invention may include reservoir. For example, a reservoir may include a medicine container and/or a standard type syringe. Optionally, a standard type syringe may be preloaded with medicine using standard equipment and/or in an aseptic room. A preloaded standard type syringe may optionally include a proximal opening. A plunger may optionally seal the proximal opening and/or protect the sterility of the contents of the syringe. A sterile needle (for example a hollow needle) may optionally be connected to the syringe barrel. For example, the hollow of the needle may be in fluid communication with the interior of the barrel. The needle may optionally be rigidly attached to the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. Optionally, the long axes of the needle and barrel of the syringe may be parallel and/or coaxial. Optionally, the needle may be mounted on the distal end of the barrel. Optionally, the needle point may be pointing in the distal direction. In some embodiments, a plunger may slide axially along the inside of the barrel to discharge a medicine payload. For example, the medicine may be discharged through the hollow needle.

In some embodiments, the force to insert the needle to the skin of a patient may range for example between 0.02 to 0.2 N and/or between 0.2 and 0.5 N. Optionally, the force required to inject the drug (for example the force on a syringe plunger) may range for example between 5 to 60 N. For example, the force required to inject the drug may depend on the injection rate and/or the viscosity of the drug and/or the syringe geometry and/or the needle dimensions.

For example, in the event of an occlusion and/or at the end of delivery, the linear force generated by the device may increase to the level of up to 60 N. A needle safeguarding mechanism (for example a needle retraction mechanism) may be sensitive to the force. For example, mechanism may include a snap that gives way at 40 N returning the needle to the retracted position. In some embodiments, a needle protection mechanism may be triggered by a linear force greater than, for example, between 10 to 60 N.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally, the pitch of the teeth and/or an associated screw may range for example between 0.5 and 2 mm. The diameter of the screw may range for example between 3 and 15 mm. The torque to power injection may range for example between 0.2 and 1.0 N*cm. The trigger torque (the torque at which the needle safeguarding is triggered) may range for example between to 0.5 to 2 and/or from 2 to 4 and/or from 4 to 10N*cm.

During injection, the linear movement of a plunger may range for example between 10-50 mm. The length of movement of the plunger may vary for example with the volume of medicine to be injected that may range for example between 0.5 to 3 ml.

In some embodiments, discharge may be driven by a torque. For example, the driver may apply torque to threaded element pushing a plunger. In some embodiments, a time of discharge may depend on the fill volume and/or viscosity. For example, the expected injection speeds may be Injection speed depend on viscosity, for example for viscosity ranging from 1 cp to 15 cp the expected injection rage may range between 30 to 40 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate. For example an expected time of discharge may range for example between 24 to 48 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 40 cp) and/or between 120 seconds and 3 minutes for larger volumes and/or viscosities.

In some embodiments, the drug delivery device may be configured to operate independently and/or be handheld. For example, the device may have a weight ranging between 10 grams to 30 grams and/or between 30 grams to 150 grams and/or between 150 grams to 500 grams. Optionally, the drug may be contained within the device. Optionally, the fluid path of the drug from the reservoir to the injection needle may be within the device. Optionally, the power supply may be within the device. Optionally, the device may be operable with one hand.

It is expected that during the life of a patent maturing from this application many relevant technologies will be developed and the scope of the terms are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An assembly for driving a plunger in a drug reservoir, the plunger dividing between a drug in a distal portion of the reservoir and a proximal opening of the reservoir; the assembly comprising:
   a telescoping shaft that extends by rotation of a driving element in a first rotational direction with respect to a distal shaft;
   a distal end of said distal shaft configured to engage the plunger; and
   an anisotropic friction element extending from said distal shaft, said friction element comprising a disk and a plurality of independent radial elements extending radially from the disk to contact an interior side wall of the reservoir, said radial elements extending from the disk toward the first rotational direction to wedge between said interior wall and said distal shaft when said distal shaft is rotated in said first rotational direction, said radial elements having respective leading edges and trailing edges, at least one of the leading edges extending radially from the disk at a first angle and a trailing edge associated with a same radial element as the at least one of the leading edges extending radially from the disk at a second angle, the first angle being steeper than the second angle.

2. The assembly of claim 1, wherein each radial element includes a virtual sprag having a long axis and wherein said long axis intersects said interior side wall.

3. The assembly of claim 1, further comprising:
   a plunger interface configured to engage the plunger; said plunger interface rotationally linking said distal shaft and the plunger when said plunger interface is engaged to the plunger.

4. The assembly of claim 1, further comprising:
   a vent for releasing gas from a space between the friction element and the plunger.

5. The assembly of claim 1, wherein said friction element is located proximal to said distal end of said distal shaft.

6. The assembly of claim 1, wherein said wedging is longitudinal such that moving said distal shaft distally with respect to said reservoir reduces a normal force between said friction element and said interior wall.

7. The assembly of claim 1, wherein a resistance to movement of said distal shaft in said first rotational direction due to friction between said friction element and said interior wall is higher than a resistance to movement of said distal shaft in a direction opposite said first rotational direction due to friction between said friction element and said interior wall.

8. The assembly of claim 1, further comprising:
a second friction element extending from a drug delivery device to contact an exterior side wall of the reservoir when said reservoir is inserted into said drug delivery device, said second friction element is configured and oriented to wedge between said exterior wall and said reservoir when said reservoir is rotated in a second rotational direction.

9. The assembly of claim 8, wherein said second rotational direction is opposite said first rotational direction.

10. The assembly of claim 1, wherein each radial element defines a radially central end and a radially outer end, the radially outer end of at least one radial element being wider than the corresponding radially central end thereof.

11. A method of advancing a plunger in a drug reservoir comprising:
Providing a telescoping assembly that extends by rotating a driver in a first rotational direction with respect to a pushing shaft mated to the driver, said pushing shaft including an anisotropic friction element in contact with a wall of the reservoir, said friction element comprising a disk and a plurality of independent radial elements extending radially from the disk, said radial elements having respective leading edges and trailing edges, at least one of the leading edges extending radially from the disk at a first angle and a trailing edge associated with a same radial element as the at least one of the leading edges extending radially from the disk at a second angle, the first angle being steeper than the second angle;
rotating said driver in said first rotational direction;
wedging said friction element between said pushing shaft and said wall as result of said rotating;
inhibiting rotation of said pushing shaft as a result of said wedging; and
unwedging said friction element to facilitate advancing of said pushing shaft.

12. The method of claim 11, wherein said wedging is substantially the only inhibiting of rotation of said pushing shaft with respect to the reservoir.

13. The method of claim 11, wherein said wedging increases a force normal to said wall and said pushing shaft relative to the normal force prior to the wedging.

14. The method of claim 12, further comprising:
reducing a normal force between said friction element and said wall of the reservoir when said pushing shaft moves in a distal direction.

15. The method of claim 11, wherein the drug reservoir includes a plunger, the method further comprising:
reducing a normal force between said friction element and said wall of the reservoir when said pushing shaft pushes distally against said plunger.

* * * * *

UNITED STATES PATENT AND TRADEMARK OFFICE
CERTIFICATE OF CORRECTION

PATENT NO. : 9,987,432 B2  
APPLICATION NO. : 14/861478  
DATED : June 5, 2018  
INVENTOR(S) : Oz Cabiri et al.

Page 1 of 1

It is certified that error appears in the above-identified patent and that said Letters Patent is hereby corrected as shown below:

In the Claims

In Claim 14, delete the number "12" at Column 24, Line 19, and insert the number --11--.

Signed and Sealed this
Twenty-eighth Day of August, 2018

Andrei Iancu
*Director of the United States Patent and Trademark Office*